US008377431B2

(12) United States Patent
Yoon et al.

(10) Patent No.: US 8,377,431 B2
(45) Date of Patent: Feb. 19, 2013

(54) **BACTERIOPHAGE OR LYTIC PROTEIN DERIVED FROM THE BACTERIOPHAGE WHICH EFFECTIVE FOR THE TREATMENT OF *STAPHYLOCOCCUS AUREUS* BIOFILM**

(75) Inventors: Seongjun Yoon, Seoul (KR); Yunjaie Choi, Seoul (KR); Se Yung Lee, Pyeongtaek-si (KR); Jeesoo Son, Seoul (KR); Sooyoun Jun, Seoul (KR); Sanghyeon Kang, Seoul (KR)

(73) Assignee: iNtRON Biotechnology, Inc., Sungnam-Si (KR)

( * ) Notice: Subject to any disclaimer, the term of this patent is extended or adjusted under 35 U.S.C. 154(b) by 110 days.

(21) Appl. No.: 12/677,990

(22) PCT Filed: Sep. 12, 2008

(86) PCT No.: PCT/KR2008/005434
§ 371 (c)(1),
(2), (4) Date: Mar. 12, 2010

(87) PCT Pub. No.: WO2009/035303
PCT Pub. Date: Mar. 19, 2009

(65) Prior Publication Data
US 2010/0254950 A1    Oct. 7, 2010

(30) Foreign Application Priority Data

Sep. 13, 2007  (KR) .......................... 10-2007-0092859

(51) Int. Cl.
*A01N 63/00*       (2006.01)
(52) U.S. Cl. ........................................ 424/93.6
(58) Field of Classification Search .................. None
See application file for complete search history.

(56) References Cited

U.S. PATENT DOCUMENTS

| 6,056,954 A | 5/2000 | Fischetti | 424/94.1 |
| 6,056,955 A | 5/2000 | Fischetti | 424/94.1 |
| 6,121,036 A | 9/2000 | Ghanbari | 436/69.3 |
| 6,264,945 B1 | 7/2001 | Fischetti | 424/94.1 |
| 6,432,444 B1 | 8/2002 | Fischetti et al. | 424/443 |
| 2003/0152594 A1 | 8/2003 | Pillich | 424/243.1 |
| 2003/0216338 A1 | 11/2003 | Merril | 436/235.1 |
| 2004/0091470 A1 | 5/2004 | Fischetti et al. | 424/94.6 |
| 2005/0260171 A1 | 11/2005 | Ghanbari et al. | 424/630 |
| 2010/0144619 A1 | 6/2010 | Yoon et al. | 514/2.7 |
| 2010/0203019 A1 | 8/2010 | Yoon | 424/93.6 |
| 2010/0203180 A1 | 8/2010 | Yoon | 514/2 |
| 2010/0267117 A1 | 10/2010 | Yoon et al. | 435/6 |

FOREIGN PATENT DOCUMENTS

| KR | 2006-55461 | 6/2006 |
| KR | 2006-73562 | 8/2006 |
| KR | 2007-82358 | 8/2007 |
| KR | 100781669 | 12/2007 |
| KR | 2007-82357 | 2/2009 |
| WO | WO 03/067991 | 8/2003 |
| WO | WO 2004/020451 | 3/2004 |
| WO | WO 2004/062677 | 7/2004 |
| WO | WO 2006/063176 | 6/2006 |
| WO | WO 2007/148919 | 12/2007 |
| WO | WO 2008/016240 | 2/2008 |
| WO | WO 2009/035303 | 3/2009 |

OTHER PUBLICATIONS

Bernhardt TG, Wang IN, Struck DK, Young R. (2002) Breaking free: "protein antibiotics" and phage lysis. Res Microbiol. 153(8): 493-501.
Bokarewa MI, Jin T, Tarkowski A. (2006) *Staphylococcus aureus*: Staphylokinase. Int J Biochem Cell Biol. 38(4): 504-509.
Genbank Accession No. AA047477, titled "Soares pregnant uterus NbHPU", entered Sep. 19, 1996.
GenBank Accession No. AY954969, titled "Bacteriophage Gl, complete genome", Direct Submission (See Kwan et al., 2005).
Genbank Accession No. AY176327, titled "*Staphylococcus* phage K, complete genome", Direct Submission (See O'Flaherty et al., 2004).
Kwan T, Liu J, DuBow M, Gros P, Pelletier J. (2005) The complete genomes and proteomes of 27 *Staphylococcus aureus* bacteriophages. Proc Natl Acad Sci USA. 102(14): 5174-5179.
Loessner MJ, Gaeng S, Scherer S. (1999) Evidence for a holin-like protein gene fully embedded out of frame in the endolysin gene of *Staphylococcus aureus* bacteriophage 187. J Bacteriol. 181(15): 4452-4460.
Loessner MJ. (2005) Bacteriophage endolysins—current state of research and applications. Curr Opin Microbiol. 8(4): 480-487.
Matsuzaki S, Rashel M, Uchiyama J, Sakurai S, Ujihara T, Kuroda M, Ikeuchi M, Tani T, Fujieda M, Wakiguchi H, Imai S. (2005) Bacteriophage therapy: a revitalized therapy against bacterial infectious diseases. J Infect Chemother. 11(5): 211-219.
Matsuzaki S, Yasuda M, Nishikawa H, Kuroda M, Ujihara T, Shuin T, Shen Y, Jin Z, Fujimoto S, Nasimuzzaman MD, Wakiguchi H, Sugihara S, Sugiura T, Koda S, Muraoka A, Imai S. (2003) Experimental protection of mice against lethal *Staphylococcus aureus* infection by novel bacteriophage phi MR11. J Infect Dis. 187(4): 613-624.
O'Flaherty S, Coffey A, Edwards R, Meaney W, Fitzgerald GF, Ross RP. (2004) Genome of staphylococcal phage K: a new lineage of Myoviridae infecting gram-positive bacteria with a low G+C content. J Bacteriol. 186(9): 2862-2871.
Skurnik M, Strauch E. (2006) Phage therapy: facts and fiction. Int J Med Microbiol. 296(1): 5-14.
Yoong P, Schuch R, Nelson D, Fischetti VA. (2004) Identification of a broadly active phage lytic enzyme with lethal activity against antibiotic-resistant *Enterococcus faecalis* and *Enterococcus faecium*. J Bacteriol. 186(14): 4808-4812.

(Continued)

*Primary Examiner* — Gary B. Nickol
*Assistant Examiner* — Khatol Shahnan-Shah
(74) *Attorney, Agent, or Firm* — Ballard Spahr LLP

(57) ABSTRACT

The present invention relates to compositions for removing a biofilm formed by *Staphylococcus aureus*, comprising a *bacteriophage*, such as Myoviridae family T4-like phage genus *bacteriophage* (Accession No: KCTC 11153BP, SAP-1) or Podoviridae family φ29-like virus genus *bacteriophage* (Accession No: KCTC11154BP, SAP-2), and lytic protein derived therefrom, that destroys the biofilm. Also disclosed are pharmaceutical compositions for the treatment of diseases caused by *Staphylococcus aureus* capable of forming biofilm.

7 Claims, 6 Drawing Sheets

OTHER PUBLICATIONS

International Search Report issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).
Written Opinion issued Mar. 20, 2009 for WO 2009/035303 published on Mar. 19, 2009 (Application No. PCT/KR2008/005434 filed on Sep. 12, 2008) (Inventors—Yoon et al.; Applicant—Intron Biotechnology, Inc.).
International Preliminary Report on Patentability issued Mar. 16, 2010 for WO 2009/035303 published on Mar. 19, 2009 (Application No. PCT/KR2008/005434 filed on Sep. 12, 2008) (Inventors—Yoon et al.; Applicant—Intron Biotechnology, Inc.).
International Preliminary Report on Patenability issued Dec. 22, 2008 for WO 2007/148919 published on Dec. 27, 2007 (Application No. PCT/KR2007/002995 filed on Jun. 20, 2007) (Inventors—Yoon et al.; Applicant—Intron Biotechnology, Inc.).
International Search Report issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).
Written Opinion issued Sep. 18, 2007 for WO 2007/148919 published on Dec. 27, 2007 (Application No. PCT/KR2007/002995 filed on Jun. 20, 2007) (Inventors—Yoon et al.; Applicant—Intron Biotechnology, Inc.).
International Preliminary Report on Patentability issued Feb. 10, 2009 for WO 2008/016240 published on Feb. 7, 2008 (Application No. PCT/KR2007/003629 filed on Jul. 27, 2007) (Inventors—Yoon et al.; Applicant—Intron Biotechnology, Inc.).
International Search Report issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).
Written Opinion issued Oct. 30, 2007 for WO 2008/016240 published on Feb. 7, 2008 (Application No. PCT/KR2007/003629 filed on Jul. 27, 2007) (Inventors—Yoon et al.; Applicant—Intron Biotechnology, Inc.).
Notice of Allowance with Examiner Interview Summary issued Jun. 1, 2011 for U.S. Appl. No. 12/378,457, filed Feb. 12, 2009 (Inventors—Yoon et al.).
Final Rejection issued Apr. 28, 2011 for U.S. Appl. No. 12/378,457, filed Feb. 12, 2009 (Inventors—Yoon et al.).
Response after Non-Final Office Action filed Feb. 25, 2011 for U.S. Appl. No. 12/378,457, filed Feb. 12, 2009 (Inventors—Yoon et al.).
Non-Final Rejection issued Oct. 26, 2010 for U.S. Appl. No. 12/378,457, filed Feb. 12, 2009 (Inventors—Yoon et al.).
Preliminary Amendment filed Dec. 19, 2008 for U.S. Appl. No. 12/308,627, filed Jun. 15, 2009) (Inventors—Yoon et al.).
Response to Non-Final Office Action filed Jul. 5, 2011 for U.S. Appl. No. 12/308,622, filed May 27, 2009 (Inventors—Yoon et al.).
Non-Final Office Action issued Mar. 3, 2011 for U.S. Appl. No. 12/308,622, filed May 27, 2009 (Inventors—Yoon et al.).
Preliminary Amendment filed Dec. 19, 2008 for U.S. Appl. No. 12/308,622, filed May 27, 2009 (Inventors—Yoon et al.).
Accession No. KCTC 11151BP, pBAD-TOPO-SAL1, 2007.
Accession No. KCTC 11152BP, *Escherichia coli* pBAD::Lysin, 2007.
Accession No. KCTC 11153BP, SAP1 bacteriophage, 2007.
Accession No. KCTC 11154BP, SAP2 bacteriophage, 2007.
Accession No. KACC 97001P, Staphloccal bacteriophage, 2006.
Arciola CR, Baldassarri L, Montanaro L. (2001) Presence of icaA and icaD genes and slime production in a collection of staphylococcal strains from catheter-associated infections. J Clin Microbiol. 39(6): 2151-2156.
Arciola CR, Montanaro L, Baldassarri L, Borsetti E, Cavedagna D, Donati E. (1999) Slime production by Staphylococci isolated from prosthesis-associated infections. New Microbiol. 22(4): 337-341.
Cisani G, Varaldo PE, Grazi G, Soro O. (1982) High-level potentiation of lysostaphin anti-staphylococcal activity by lysozyme. Antimicrob Agents Chemother. 21(4): 531-535.
Costerton JW, Lewandowski Z, DeBeer D, Caldwell D, Korber D, James G. (1994) Biofilms, the customized microniche. J Bacteriol. 176(8): 2137-2142.

Cramton SE, Gerke C, Schnell NF, Nichols WW, Götz F. (1999) The intercellular adhesion (ica) locus is present in *Staphylococcus aureus* and is required for biofilm formation. Infect Immun. 67(10): 5427-5433.
Graham S, Coote PJ. (2007) Potent, synergistic inhibition of *Staphylococcus aureus* upon exposure to a combination of the endopeptidase lysostaphin and the cationic peptide ranalexin. J Antimicrob Chemother. 59(4): 759-762.
Gründling A, Missiakas DM, Schneewind O. (2006) *Staphylococcus aureus* mutants with increased lysostaphin resistance. J Bacteriol. 188(17): 6286-6297.
Kusuma C, Jadanova A, Chanturiya T, Kokai-Kun JF. (2007) Lysostaphin-resistant variants of *Staphylococcus aureus* demonstrate reduced fitness in vitro and in vivo. Antimicrob Agents Chemother. 51(2): 475-482.
Mah TF, O'Toole GA. (2001) Mechanisms of biofilm resistance to antimicrobial agents. Trends Microbiol. 9(1): 34-39.
McKenney D, Pouliot KL, Wang Y, Murthy V, Ulrich M, Döring G, Lee JC, Goldmann DA, Pier GB. (1999) Broadly protective vaccine for *Staphylococcus aureus* based on an in vivo-expressed antigen. 284(5419): 1523-1527.
O'Gara JP, Humphreys H. (2001) Staphylococcus epidermidis biofilms: importance and implications. J Med Microbiol. 50(7): 582-587.
Resch A, Fehrenbacher B, Eisele K, Schaller M, Götz F. (2005) Phage release from biofilm and planktonic *Staphylococcus aureus* cells. FEMS Microbiol Lett. 252(1): 89-96.
Sass P, Bierbaum G. (2007) Lytic activity of recombinant bacteriophage phi11 and phi12 endolysins on whole cells and biofilms of *Staphylococcus aureus*. Appl Environ Microbiol. 73(1): 347-352.
Schuch R, Nelson D, Fischetti VA. (2002) A bacteriolytic agent that detects and kills *Bacillus anthracis*. Nature. 418(6900): 884-889.
Severance PJ, Kauffman CA, Sheagren JN. (1980) Rapid identification of *Staphylococcus aureus* by using lysostaphin sensitivity. J Clin Microbiol. 11(6): 724-727.
Vybiral D, Takác M, Loessner M, Witte A, von Ahsen U, Bläsi U. (2003) Complete nucleotide sequence and molecular characterization of two lytic *Staphylococcus aureus* phages: 44AHJD and P68. FEMS Microbiol Lett. 219(2): 275-283.
Waldvogel FA. (2000) Infections Associated with Indwelling Medical Devices, pp. 55-88, 2000, ASM, Washington, DC.
Walencka E, Sadowska B, Rózalska S, Hryniewicz W, Rózalska B. (2006) *Staphylococcus aureus* biofilm as a target for single or repeated doses of oxacillin, vancomycin, linezolid and/or lysostaphin. Folia Microbiol (Praha). 51(5): 381-386.
Wu JA, Kusuma C, Mond JJ, Kokai-Kun JF. (2003) Lysostaphin disrupts *Staphylococcus aureus* and *Staphylococcus epidermidis* biofilms on artificial surfaces. Antimicrob Agents Chemother. 47(11): 3407-3414.
International Search Report dated Mar. 20, 2009 for PCT/KR2008/005434.
Written Opinion dated Mar. 20, 2009 for PCT/KR2008/005434.
International Preliminary Report on Patentability dated Mar. 16, 2010 for PCT/KR2008/005434.
Notice of Allowance mailed Sep. 4, 2012 for U.S. Appl. No. 12/378,365, which was filed on Feb. 2, 2009 (Yoon et al.—Inventors) (7 pages).
Response to Non-Final Office Action filed Jul. 5, 2012 for U.S. Appl. No. 12/378,365, which was filed on Feb. 2, 2009 (Yoon et al.—Inventors) (8 pages).
Issue Notification mailed Jul. 11, 2012 for U.S. Appl. No. 12/308,627, which was filed on Jun. 15, 2009 (Yoon et al.—Inventors) (1 page).
Response to Rule 312 Amendment mailed Jul. 6, 2012 for U.S. Appl. No. 12/308,627, which was filed on Jun. 15, 2009 (Yoon et al.—Inventors) (2 pages).
Amendment in Response to Notice to File Corrected Application Papers mailed Jun. 29, 2012 for U.S. Appl. No. 12/308,627, which was filed on Jun. 15, 2009 (Yoon et al.—Inventors) (4 pages).
Response to Notice to File Corrected Application Papers mailed Jun. 29, 2012 for U.S. Appl. No. 12/308,627, which was filed on Jun. 15, 2009 (Yoon et al.—Inventors) (5 pages).

(A)

(B)

SEQUENCE LISTING

```
<160> NUMBER OF SEQ ID NOS: 31

<210> SEQ ID NO 1
<211> LENGTH: 776
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 1
tatgggtata cacaaattat atcaacaatc tgaccaatgg tattatggtc atagatgtca      60
acattgtgat tatttaaatg aaatgagtta taatgattac aaccctgata atcttgaaga     120
```

-continued

| | |
|---|---|
| aagtgggaat atgttatgtg ttaaccctga aggtgtagat gaacaggcta aaacagtaca | 180 |
| gaatggtagt taccaatttg tttgtcaaaa atgcggtaaa ccactagata gatggtataa | 240 |
| tggtgagtgg cattgtaagt atcctgagcg tacaaaaggt aataaggggg tacgaggata | 300 |
| cctaataaca caaatgaacg ctgtatggat ttctgctgat gaattaaaag aaaaagaaat | 360 |
| gaatacagaa tctaagcaag cgttttacaa ttatattttg ggttatccat ttgaagatgt | 420 |
| ttaactgaga gttaatgaag aagacgtttt atggtaacaa atcacctatt gcagaaacac | 480 |
| aattaatgaa acgagataga tattctcata tagctaatgg tatagattgg ggaaatactc | 540 |
| attggataac tgttcatggt atgttaccta atggtaaggt agacttaata cgattattct | 600 |
| ctgttaaaag atgaccagac ctgatttagt gaagcagatt tagaaaaatc atttggggaa | 660 |
| atatctagta cgacctgata tataatgcga tacggagatc agaaacatgg tctaaactca | 720 |
| tatcatttga aagataaagt atttgatgta cgtataatct tcctcttagt ctacag | 776 |

<210> SEQ ID NO 2
<211> LENGTH: 1424
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 2

| | |
|---|---|
| gaagctaaca aggcaattca aaaaagatgt agattcaggt aaggcaattg aactaggtga | 60 |
| tgtagctatt atagatacag cattaagtat tattctttca ggtaacgagt tccaaggaag | 120 |
| tattcgttta tgctaaaaaa agacttgaag aaaagaaag aattagaaaa gaagaagaag | 180 |
| agaaacttaa taacttataa aagggaagaa ttatgagact atataaaatg aggtatcata | 240 |
| attgaaaaag aaaccacaag gcaatgagat aatcataacc ataataacgg ttatgatagc | 300 |
| aatatttgta gtcattatga ccatattttt taataaatac caagatgcta agaagataa | 360 |
| agatagatat cagagattag ttgagatttta aaaaaagca gatgataatg atggagagac | 420 |
| taaaagaaa tacgtaaaaa gattaaataa agctgaagaa gaacttaaaa aagtaaagaa | 480 |
| agaaacaaat tataaagact ataataagaa gtcaaataaa gaaagacaaa aggaagataa | 540 |
| agaaactaga gagaaaatat atgatgtaac tggtgatgat gacttaatat tagtaaaaaa | 600 |
| taatattgag tttagtgata aggtagataa acctgaaata cttattagtg aagatggaat | 660 |
| tggtacgata actgtcccta caaacagtgg ttatgaaaaa caaacagtag gttctattat | 720 |
| tactagtgta ttaggttccc cgttcttatc aactgattca ccggtataga tagttaggta | 780 |
| tcatatagtt atgttatccc aaatacagta gatagtatag tagagataca aatacttcta | 840 |
| ctgataatgt actaaaggat aatccctatt ataacaaatc ccagttgaac ccaaccacac | 900 |
| cttcagatat attacctcct attgataatc ccgtcagttc ctatattacc tgaaaaccct | 960 |
| gtagacaata attcaggaaa tatagataat acggataatc caaaccctcc cacctccagg | 1020 |
| atataccaga tgaagatgga ggtagaggcc caggtggtgg aggtaatgtt gaaccccccc | 1080 |
| caacggaaga accttcagat aacggtaata caggaggagg agattgggaa gaaaaacctg | 1140 |
| acccaggaga agagccatca gataatggta atacaggaga caatgaagga gaggtaactc | 1200 |
| ctgaacctga ccctacacct tctgagcctg aacaacctaa tgaaaaccct aatgagggta | 1260 |
| atggtaatga agaaaaacca tccgaaccat cagataatcc tgatgaaaat ggaggatggg | 1320 |
| aaactgagcc ttccgaacct gaacacactt ctgagccgga cgataaggtg gacgaagagg | 1380 |
| ataaaaacga agatacaaca gaggataaac aacctacaga acaa | 1424 |

<210> SEQ ID NO 3
<211> LENGTH: 702
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 3
ctaaagaacc tgaaaaggtt actgaggaag atgctaaaga agcacaagag caaggtgaaa        60
aagttgaatc tgaagaggta acagaggaca ctgaagatga ggaagttgaa aaatcagcta       120
aagaatcaaa agaccctgta gaccaaaaag atactaaaac agaaaataaa gacaacgaga       180
aacgtaaaaa taaaaagat aaaaagaag attctgaatc tgatgatgaa gacaaagata        240
ctgacgatga taaagataag aaagaagata agaaggaaaa aacttctaaa tcaatttctg       300
atgaggatat cacaacagta tttaaatcta tcctaacatc ttttgaaaac ttaaataagg       360
gagaaagaaa actttgctac taaagacgat ttaagtgaag ttagtaaatc tattaatgaa       420
gttatcagca aaaatttctg aaatccaatc tgaaagatgt ttctaaatca gtagacactg       480
atgaagaaga agctgtagaa aaatcagtaa catctacaaa tggggagcaa gaaaaagtag       540
aaagttatgt ttctaaatca gtagacactg aagagcaagc tgaaactggt gaagcaaatc       600
agagatgctg agagtacaga gatacacatt aagatagtca gagaagacta gtcatgatct       660
ataagcacag ctaagaccta gagcttctaa acatgactta ca                         702

<210> SEQ ID NO 4
<211> LENGTH: 772
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 4
caacagccaa aaaagatgaa ataagtaaa gggtgaatta aatggttaac tcaatgtttg         60
aggggactta gacctttgaa aaatcataaa ctatgaatat cttatcatcc tagtggtaat       120
cctaaacata tagacgtaag tgagatagat aacttaacat tagctgatta tggatggtca       180
cctgatgcag ttaaagctta tatgtttggt attgtagtac aaaaccctga tacaggacag       240
cccatgggtg atgagtttta taaccatata ttagaaagag cagtaggtaa agctgagaga       300
gcgctagata tttctatact acctgatact caacatgaga tgagagatta tcatgagaca       360
gagtttaata gttatatgtt tgtacatgct tacagaaaac ctatattaca ggtagagaac       420
ttacagctac aatttaatgg tagacctata tataaatacc ctgctaactg gtggaaagta       480
gagcatttag caggtcatgt tcaattgttc cctacagcac ttatgcaaac aggacaatca       540
atgtcatatg atgctgtatt caatggatac cctcaattag caggtgtata cccaccatca       600
ggagcaacct ttgcacctca aatgatacga ctagaatacg tatcaggtat gcttccacgt       660
aaaaaagcag gtagaaataa accttgggag atgcctcctg agttagaaca gctagttata       720
aaatatgcat tgaaagaaat ataccaagta tggggtaact taatcattgg tg               772

<210> SEQ ID NO 5
<211> LENGTH: 784
<212> TYPE: DNA
<213> ORGANISM: Artificial Sequence
<220> FEATURE:
<223> OTHER INFORMATION: Description of Artificial Sequence: Note =
      Synthetic Construct

```
<400> SEQUENCE: 5
aagaaataga taaattaaaa tatcaagata agcaagaaaa agaacaagta attaacaaag      60
ttattaaagg tgttaatgat acttgggaaa aagaatataa ctttgaagaa ttagatttaa     120
gatttaaagt taaaattaaa ttacctaatg cacgagaaca aggtaacata tttgcgttac     180
gttctgctta cttaggtggt atggatatgt atcaaacaga ccaagtaatt agagcatacc     240
aaatgttagc tacattacaa gaagtaggta ttgaagttcc taaggaattc caagaccctg     300
atgatatcta taacttatat cctttaactg ttatgtatga agattggtta ggatttttaa     360
actcctttcg ttactaatag tatagaaaca ttagataaag atatagaacg attgggtggt     420
atggaatcaa ttgttaaaca acctttatct agaaatctat gggctattat gaaagagttt     480
aatgttttgc ctactgagca agatttaag gatttagacg attatcaaat agagtttatt      540
attggtaata tgaataggga tgtttatgaa cataataaac aacttaaaca agctcaaaaa     600
ggtggaaaat tcgacagtca atttgaagat gatgatagta gttggtggaa tgaatctcat     660
gaagactttg acccggtacc tgatttctta gatgccgatg acttagcaca acagatggaa     720
gctaaattat ctgatagaga taaggaagaa agagctaaga gaaatgatgc ggagttaaat     780
gatg                                                                 784

<210> SEQ ID NO 6
<211> LENGTH: 761
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 6
gaaggactca ctacacaaca tcttgctatg atggaataca ttagaagaaa acaagaagaa      60
ttagatgatg aagtaggaaa tggtaaaact agtgaagatg atgctactat atcacaagag     120
agcgttaata aagcactaga agacctagat gatgactggt atatgtaaag ggtggtaggt     180
gatactacca tccttatttt tttaaaatgg atggtgaata atgatggcaa tgaatgacga     240
ttatagattg gtcttatccg gtgatagttc ggatttagag aatagtctga aggcaataga     300
actttatatg gattccctag aatctaaaaa tattgatgcc cctttagaca atttcttaaa     360
gaaattaaaa gtaattgcta agaagttaa aaatgtacag aactcaatgg ataaacaaga     420
aggtaaatct gtcatatctt ctaaagatat ggatgaatct attaaatcca ctcaatctgc     480
tacaaagaat ataaatgaat aaagaaagc cttagatgac cttcaaaaag aaaatatatc     540
taaaggtatt gcacctgacc ctgaagttga aaaagcatat gctaagatgg gtaaagttgt     600
agatgaaact caagaaaaac ttgagaaaat gtcttcacaa aaaataggct cagacgctag     660
tatacaaaat agaattaagg aaatgaaaac cttaaatcaa gtaacagaag atataataag     720
ataagtaaag attctagtgc tactaaagac tatactaaac g                        761

<210> SEQ ID NO 7
<211> LENGTH: 1472
<212> TYPE: DNA
<213> ORGANISM: Artificial Sequence
<220> FEATURE:
<223> OTHER INFORMATION: Description of Artificial Sequence: Note =
      Synthetic Construct
```

<400> SEQUENCE: 7

| | |
|---|---|
| taaatagtac tgacatgttg aaaatggcta cttcatatga agcatctgta ggacataaaa | 60 |
| gtgatgagga tacaatggca ggaactaaac aacttgctat tggaggacgt tctttaggta | 120 |
| ttaaagacca agaagcttat caagagtcta tgggtcagat aatgcatact ggtggagtaa | 180 |
| attccgataa catgaaggag atgcaagatg cattcctagg cgggattaaa caatcaggta | 240 |
| tggttggtcg tcaagatgaa caacttaaag cattaggttc tatagctgaa caatcaggag | 300 |
| aaggaagaac tttaactaaa gaccaaatga gtaatcttac tgctatgcaa tctactttg | 360 |
| cagagtcagg aagtaaagga ttacaaggtg aacaaggtgc caatgctatt aatagtatag | 420 |
| accaaggact taaaaatggt atgaatagtt cttatgctcg tatagcaatg ggatggggaa | 480 |
| cacagtacca aggtcttgaa ggtggatatg atttacaaaa acgtatggat gaaggtatat | 540 |
| ctaaccctga aaacttgaca gacatggctg atatggctac tcaaatgggt ggtagtgaaa | 600 |
| aagaacaaaa atacctattc aatagaagta tgaaagaaat aggtgctaac gattaactat | 660 |
| ggagcgaatc tgatgagata ctttaaagat gctcgaatcc ggaaaattat ctaaagaaga | 720 |
| gttagctaaa aaagctaaga aaatggaaaa agaaggtaaa aaagaaggag aagataacgc | 780 |
| cactgattat aaagaatcta atcaggaaa aaatgaccaa aataaatcta agactgatga | 840 |
| taaggcagaa gatacttatg atatggctca accattaaga gatgctcata gtgctttagc | 900 |
| agggctacct gctcctatat atttagcaat aggagctatt ggagcattta cagcatcact | 960 |
| aattgcatct gcaagtcaat ttggggcagg tcatttaata ggtaaaggag ctaaaggact | 1020 |
| tagaaataaa tttggcagaa ataagggtgg tagctccgga ggtaacccta tggcaggagg | 1080 |
| aatgcctact ggaggaggtt cacctaaagg cggaggctct cctaaaggtg gcggtactcg | 1140 |
| ttctactgga ggtaaaatac ttgatagtgc taaaggatta ggaggattcc tagtcggtgg | 1200 |
| agcaggatgg aaaggtatgt ttggtggaga atctaaaggt aaaggattta acaaacatc | 1260 |
| taaagaagcc tggtcaggta ctagaaaagt atttaacaga gacaatggta gaaaagccat | 1320 |
| ggataaatct aaagatatag ctaaaggtac tggtagcggt cttaaagata tttataatga | 1380 |
| tagtatattt ggaaaagaaa gaagacaaat ctaggagata aagctaaagg ttttggtgga | 1440 |
| aagctaaagg tctctatggt aaatttgctg at | 1472 |

<210> SEQ ID NO 8
<211> LENGTH: 763
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 8

| | |
|---|---|
| taaccgacat tacaagtatc aatgtacttg gtatgcttat aatagaagag gtcaattagg | 60 |
| cattcctgtg cctttatggg gggatgccgc cgactggatt ggcggtgcta aaagtgcagg | 120 |
| ttatggtgta ggtagaacac taaacaagg agcttgtgtc atatggcaaa gaggagttca | 180 |
| aggcggtagt gctcaatatg gtcacgtagc ttttgttgag aaagttttag atggaggtaa | 240 |
| aaaaatattt atctctgaac ataactacgc tactcctaat ggatatggta ctagaacaat | 300 |
| agatatgagt tcagctatag gtaagaatgc tcaattcatt tacgataaga ataaaggag | 360 |
| gatagtctat ggcaacagat aaagaagcta agatgttat tgataaattt atagataatg | 420 |
| tatttaattt tgatgtactt acaaaagaaa gaataaaaga aaagatgaa gaaattaaaa | 480 |
| aaataactac agatgatatg tatgaaaaag ttgttatat acgaccttat gttggagtga | 540 |

| tacaaagcct taaccctcaa catgtacaat atgaatcatt ttctaataat ggttacgata | 600 |
| tagaagcaga attaagtttt aggaaagtaa gttatttagt tgataaaggg tctatacctta | 660 |
| cagattcttt atccacttta acagttcatt tagtagaaag aaaccaggag ttattaatag | 720 |
| attactttga tgagatacaa gatgtgttgt atggggaata tat | 763 |

```
<210> SEQ ID NO 9
<211> LENGTH: 696
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
```

| gatgaagagg tgtatattta atggtagtaa gatttccaat cttccatggg gagaagtcta | 60 |
| aaaagagtag attcagatga cttaaatgta aagggttag ttttagctac agttagtaaa | 120 |
| attaattata agtatcaatc agtagaagtt aaagttaata acttgactttt aggaagccgt | 180 |
| ataggtgatg atggtagctt agctgtacct tatcctaaat ctttcatagg tagaacacct | 240 |
| gagggaagtg tatttggtac aaaaccactt attactgaag gttctgtagt attaataggg | 300 |
| ttcctaaatg atgatataaa tagtcctata atcttgagtg tttacggtga taatgaacaa | 360 |
| aataaaatga ttaatacgaa tcctttagat ggaggtaagt tgatacaga agtgtttac | 420 |
| aaatacagta gttcactata tgaaatttta ccatctttaa attataaata tgatgatgga | 480 |
| gaaggaacaa gtattagaac ttataatggt aaatcattct tctctatgac atcaggtgaa | 540 |
| gaagagaaac cacaggcaac agattttat actggaactg agtatcaaga tttatttact | 600 |
| tcctattacg gtaataaaac attgattgaa cctagaatac aaaaggctcc taatatgtta | 660 |
| ttcaaacatc aaggagtttt tatgatgat ggtacg | 696 |

```
<210> SEQ ID NO 10
<211> LENGTH: 754
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
```

| agaggtcatc gagaataaaa actatgtacc acctaaaatc aataatggtg atgaggattc | 60 |
| ccaacaaaat actgtaccta agaacaata tgatagttta aaagaagagc tagaacttat | 120 |
| gagacagcaa caagaagcta tgatgaaaat gcttcagcaa ctcttaggtc aaaaggggta | 180 |
| ataataaatg gcattaaatt ttactacaat aacagaaaac aatgttatta gagacctgac | 240 |
| tgttcaggtc aataacattg gagaagagtt aacaaaagaa agaaatatat ttgacattac | 300 |
| ggatgattta gtttataatt ttaataagtc acaaaaagtt aaattaacag atgataaagg | 360 |
| tttatctaaa tcttatggta atataactgt aattagggat ataaaagaac caggttacta | 420 |
| ttatataaat gcaagaacat tagctacact attagataaa cctgatatag aatccataga | 480 |
| tgttttactt catgtattac ctttagattc atctagtaga gtaatacagc atttatatac | 540 |
| gttgtctact aacaataatc aaattaagac attatataga tttgtttcag gtagctctag | 600 |
| ttcagaatgg cagtttataa ctggattacc tagtaataaa aatgctgtta tttcaggaac | 660 |
| taatatttta gatatagctt caccaggtgt ttactttgtt atgggaatga caggaggaat | 720 |
| gcctagtggt gtagattcag gttttctaga tttg | 754 |

-continued

<210> SEQ ID NO 11
<211> LENGTH: 665
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 11

```
gttaaactta aaaaaacata atgcacattt ccaaaaagtt gttagagaaa agaatgaaaa      60
gaaatatgat aaatatcaag atatgagaga cttttttagat tcagtgactg ttatgatagt    120
tgatgaagca catcactcta atcagattc gtggtatata atctaatga catgtgaaaa      180
agctttgtat aggattgcat taacgggttc tatagataaa aaagatgaat tactatggat    240
gagattgcag gctctatttg gtaatgttat tgcacgaact actaataagt ttttaattga    300
tgaaggtcat tctgctagac aacaataaa tattatacc gtagctaatc ctaatgacat     360
agatagaatt gatgattaca gggaagctta tgataaaggt ataacaaata atgatttag    420
aaataaactt attgcaaaac taacagaaaa gtggtataat caagataaag ggacattgat    480
tattgtaaac ttcatcgaac atggagatac aatatcagaa atgttaaatg atttagatgt    540
agagcactac ttcttacatg gagaaataga ctctgaaacc cgtagagaaa aattaaatga    600
tatgagaagt ggtaagctta aagtaatgat agctacatca cttattgatg agggtgtaga    660
tatat                                                                 665
```

<210> SEQ ID NO 12
<211> LENGTH: 789
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 12

```
attcaaatcc ttttaatgac tttgatgtaa acagtgttga tgattcacaa gtacctttg      60
agacacaacc tcaaaacaca caacaagcac ctgaaccaca acaaactact caggagcctc    120
caaaacaaaa acaaacacaa agtattgacg atgtattagg tggtctagac ttagataacc    180
tataagatat agagtgcctt agagcactct tttatttgag atataattac taggaggata    240
ttaaatggca agagcaaaaa aaggtaaaga agtagattta acagatttaa atacaattga    300
tttaggtaaa gaattaggat taacattatt atcagataca aatagagcag atattaagaa    360
tgttataccct acaatggtac ctcagtatga ctatattta ggtggaggta taccgttagg    420
tagattaaca gaggtttatg gtttaactgg tagtggtaaa tcaacatttg cagttcattt    480
gtctaggatt gcaacacaat aggtgttat taccatttgg attgatattg aaggaacagc    540
agacaataat cgtatggaac aacttggagt agatgtttca aaattattct ctattcaatc    600
aggagaaggt agacttaaaa atacagtaga attatctgta gaggctgtag gtaaagaatt    660
agagtactgg attgacacat ttaatgaaaa gatacctgga gtaccattg tgtttatttg     720
ggactcacta gagctacacg aactcagaaa gagattgacg gcggtattga tgagaaacaa    780
atgggtctt                                                             789
```

<210> SEQ ID NO 13
<211> LENGTH: 685
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 13

| | | | | | |
|---|---|---|---|---|---|
| tcctaaggaa | gacggagcag | acgtatcagc | agaataatat | agataaagga | tggtaaattt | 60 |
| ggctaagtta | aatttataca | aaggtaatga | gttactaaac | agcgtagaga | aaacagaagg | 120 |
| aaaatcaaca | atcacgattg | agaatttaga | tgctaacaca | gattcccta | aaggtacttt | 180 |
| taaagtatca | ttctcaaatg | attcaggaga | atcagagaag | gtcgatgtcc | ctcagtttaa | 240 |
| gacaaaagca | attaaagtta | tttcagttac | ccttgacgtt | gatagtttag | accttacagt | 300 |
| tggagatact | caccaactat | caacaactat | cacgcctagt | gaagcatcta | acaaaaatgt | 360 |
| gtcatttgaa | tcagacaaat | caggtgttgc | tagtgtaaca | tcagaaggat | taattgaagc | 420 |
| agttagtgca | ggaacagcta | atattactgt | aactactgag | gatggtagtc | atactgatat | 480 |
| tgttgcggta | acagttaagg | aacctattcc | tgaagcacct | acagatgtaa | cagttgaacc | 540 |
| tggtgaaaat | agcgcagata | ttactgcata | ggaggacaat | aaagaatgga | aaagacatta | 600 |
| aaagtttata | gtaatggtga | agttgtaggc | tctcaagtag | ctaataacga | tggagctact | 660 |
| acagtatcta | ttacaggctt | agaag | | | | 685 |

<210> SEQ ID NO 14
<211> LENGTH: 700
<212> TYPE: DNA
<213> ORGANISM: Artificial Sequence
<220> FEATURE:
<223> OTHER INFORMATION: Description of Artificial Sequence: Note= Synthetic Construct

<400> SEQUENCE: 14

| | | | | | |
|---|---|---|---|---|---|
| tctcacccat | ctacatctac | aaaagtattc | cattccatat | ctatacaaga | acgttcacta | 60 |
| ctttctataa | aggcatttaa | atcggcatat | aattgaacaa | aaaaagacat | atcatagttc | 120 |
| caatacttag | gttcatttct | tcctaatttt | ttattcattt | ttttatactt | tctatttctc | 180 |
| tttaacccaa | aaacttcttt | ttcaaaatca | tttaatttta | aacctttaaa | atattttttc | 240 |
| ttcatatcta | atcctccaat | ttaataagtg | gtaaatctat | atctctaaat | acagaaccta | 300 |
| cgtcacatag | cagtatatca | ttatgttctt | ctacttcacc | actactagta | ggtgtatgac | 360 |
| cacatacata | tataaatcca | tctttttctag | gttggaagtc | tctagaccat | attaactggt | 420 |
| ctactgtttg | ctcttctata | ggtttccaac | taactcccccc | tgaatgggaa | aatatatact | 480 |
| taccttcttt | ataatacctt | ctacaattaa | ccataaatat | tttaaatttt | ctataatctt | 540 |
| cagattcttt | aagtttcttt | agttcacttt | taataaaatc | ataatgattt | cttaaattat | 600 |
| cttctacact | tttatatttt | aaagttacag | tactaacacc | gtaagagtta | agtgtttcta | 660 |
| tacaatacct | tgataaccat | tcaatatcat | agatacttaa | | | 700 |

<210> SEQ ID NO 15
<211> LENGTH: 789
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 15

| | | | | | |
|---|---|---|---|---|---|
| gaatggtacc | cgatgaacca | gctgttggcg | ttgcacaaat | aatacccatc | gcagcattga | 60 |
| cttcatttgt | tgcaatggca | cctttgactg | catcaatcat | ttcatatcca | gacaaagcat | 120 |

-continued

| | |
|---|---|
| gatgtgtttc attataatca cgtagtttag cagcgtcatg accagtgtag cccgttacac | 180 |
| tttcaacgcc atcacctgtc gtcccttga ttactgcgtc tcgcatgaca tctaaatttt | 240 |
| gtttcatttg cgctcgcact tcatcacgtg atttaccgct taattccatt tcttctttaa | 300 |
| ccatgatatc cgcaaatgac atattatttt ctacggcata atctatagtc tctctaattg | 360 |
| aatcaaacat gtttattccc cctctaattt ataggaaa cgtttacgtc actgtatttc | 420 |
| tctttaattg tatttaatat cgattctgag attgctttat ttaatggtat tacaaccaag | 480 |
| catttatctt catctatctt aataaattca tctttacagt ctaatttcat atcgttgata | 540 |
| tcattaatga aatgatttac ttgtgcttta gtcatatttc cgtcaacaac taaaattggt | 600 |
| aatccatgat ttaaatctac ttctagtcca tttatgaa tacctttaat tttaattgta | 660 |
| ccaccaccga ttgaataccg atatttcata tagcaccatc atacgagatg attatatagc | 720 |
| acagtttgga tgttgacata ctatcgcttc tcttcgatga tatctatttt aataccatca | 780 |
| tcagctgca | 789 |

<210> SEQ ID NO 16
<211> LENGTH: 710
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 16

| | |
|---|---|
| gctaaatgtc acgatacatg cgtgacgacc ccaatcagtg catttgtacc atatagtgta | 60 |
| ctggatatgc gctataaatc aatttgcgtc aatggctcaa tacaaactgc aaatgctttg | 120 |
| acggtccacc aatgtttaat tttcggaata aaataaggtt aacaaatgag ctacctgtac | 180 |
| atgttagtgc tccaatagcc ataggaacac ctgtcagtcc taataaactt gttaatacca | 240 |
| ttgaacttag cggtgtcata cctgtaacag gaatcactag tcctaaaatg accgctaatg | 300 |
| catatggatt gttatcacct accgcagtaa cagcactacc tatttgtttt aatgttgcta | 360 |
| gcacaccagg tgtaatgatt gatgcaagtc cgaaagcaat tgctggtgca ataagatca | 420 |
| ccacaattaa gtccaagcct tctggaactt tcttttcaat ccatttaatt aaaaaagcta | 480 |
| cgccataagc tgcaatgaat gctggtaata atttaaagtc atgtaatact aaaccaacaa | 540 |
| tgaccgcaaa tactggtgca acgcctaagt ttaagcacgt tagaatacct actgcgatac | 600 |
| cgcttaaact tcctgctaaa tccccaatat cttgtagaaa tttaatatca aatacgccac | 660 |
| caatggcata acttaagaat gcttgtggta gaaatgtcgc acaagctgca | 710 |

<210> SEQ ID NO 17
<211> LENGTH: 762
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 17

| | |
|---|---|
| gagacaaagc taaagaatta aatatcgaac cattggcagt gcttgatggc tttggaagtc | 60 |
| atggtgtaga tccttctat tatgggtatc gcaccagttg gcgctgttga aaaggctttg | 120 |
| aaacgtagta aaaagaatt aagcgatatt gatgtatttg aattaaatga agcatttgca | 180 |
| gcacaatcat tagctgtaga tcgcgaatta aaattacctc ctgaaaaggt gaatgttaaa | 240 |
| ggtggcgcta ttgcattagg acaccctatt ggtgcatctg gtgctagagt tttagtgaca | 300 |

| | | |
|---|---|---|
| ttattgcatc aactgaatga tgaagtcgaa actggtttaa catcattgtg tattggtggc | 360 | |
| ggtcaagcta tcgctgcagt tgtatcaaag tataaataat aagaaaacag gttatcacaa | 420 | |
| cagtattaat tacatgttgg cataacctgt ttttatttgt ttatggattt attgggtaat | 480 | |
| attagtcatt tgatggttta attgcaaatg ctctaacagg gaacccaggt gcatcttttg | 540 | |
| gtttagggct gatagcgtaa atgatggcgc cacgagttgg taattgatct aaattagtta | 600 | |
| ataactcgac ttggtattta tcctgaccaa gaatataacg ttcgccaact aaatcaccat | 660 | |
| tttttacaac gtccacagat gcatcggtat cgaatgtttc atgaccaaca gcttcaacac | 720 | |
| ggcgttcttc aattaagtac ttcaaagcat ctaatcccca ac | 762 | |

<210> SEQ ID NO 18
<211> LENGTH: 673
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 18

| | | |
|---|---|---|
| acgttctact aaatgcatca tattaacagg tgataataca agatgtttct gaaatggaat | 60 | |
| aagccctgtc gctgcaatga atacgcctaa aaatccaggg atgtaatgga tactttgcgg | 120 | |
| tagtactaat gatagaaatg ataaaaatga atcacaaaag gctacggtcg caaaagcttg | 180 | |
| acatgtacgc ttatcgccat aatctaatcc tgtacgtata tgtaataaat actgtaatcc | 240 | |
| gatacttaag tacataattg ccacgcataa gaagaatggg aagaatgtct tttcaaagtc | 300 | |
| cggatatagg ctgttagata ggaagaccat gataaacata ttaaacatca taaacgaaac | 360 | |
| gtctttgaat gtaacttgac caaatcgatt tgtaaaaaat gtttgatgag accacattaa | 420 | |
| ccataagaac aaactcatga cgatgtattt gaaaaacaaa tcagctgaaa tggaaccatt | 480 | |
| ttgtgttgtt aaaatcacat gtgcaatttt ttgaatggca tagacgaaaa ttaaatcaaa | 540 | |
| gaacaactca tggaatcctg cacgcttttc agctaaatgt tttggtgtta atgcattaac | 600 | |
| cataaaattt taactccttt aagatgtgta attaatttac taagtatact atttattttt | 660 | |
| tctagtgaat agg | 673 | |

<210> SEQ ID NO 19
<211> LENGTH: 766
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 19

| | | |
|---|---|---|
| cacatttagt acaaaataac gacattatcg ttattacatg caattatcgt ttaggcgcac | 60 | |
| taggatattt agactggtca tattttaata aagattttca ttccaataac ggactttcag | 120 | |
| atcaaatcaa tgtcataaaa tgggtgcatc aatttattga atccttcggt ggcgacgcta | 180 | |
| ataacattac tttaatgggt cagtctgcag gcagtatgag cattttgact ttacttaaaa | 240 | |
| tacctgacat tgagccatac ttccataaag tcgttctgct aagtggcgca ctacgattag | 300 | |
| acacccttga gagtgcacgc aataaagcac aacatttcca aaaaatgatg ctcgattatt | 360 | |
| tagatacaga tgatgttaca tcattatcga cagatgatat tcttatgctg atggcgaagc | 420 | |
| taaacaatc tcgaggacct tctaaagggc ttgatttaat atatgcgcct attaaaacag | 480 | |
| attatataca aaataattat ccaacaacga aaccaatttt tgcatgtaat acaaaagatg | 540 | |

-continued

| | |
|---|---|
| aaggcgatat ttatattact agtgaacaga aaaaattatc gccgcaacgc tttatcgaca | 600 |
| ttatggaatt aaatgatatt cctttaaaat acgaagatgt tcagacggcg aagcaacaat | 660 |
| ctttagcgat tacacattgt tatttcaaac agccgatgaa gcaatttta caacaactca | 720 |
| atatacaaga ttcaaacgca aaactatggc ttgctgaatt tgcatg | 766 |

<210> SEQ ID NO 20
<211> LENGTH: 654
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 20

| | |
|---|---|
| aaaacaacga ttaatcctaa tgcgccaatg atggcactcg tatacgtgat agcttgaaca | 60 |
| gaaacatgtg tcatgaccaa gcctccaata atgccaccaa caccaatacc agcgtttaaa | 120 |
| ctagacatgt tccaactcat tacttggctt gtgtcgcctt caacatgttg aatcacaccg | 180 |
| ctttgcactg ctggattagt actccattgc atgatattcc aaataaatag tcctgctaac | 240 |
| aatagacctg aaccaggtaa gattaaattc ataagtaaca tcatgacgat aaaaatagaa | 300 |
| accgaaatca ttaaccaacg cttacttgta attttatcgg agaatatacc acctaatgat | 360 |
| gttccaataa cgccagcgat tccatttact agaagtgcta atgaaacgaa tgacatatca | 420 |
| tgaccattag ataaaataag tggatttata aagacgaatg tcactgagtt tgcaatcaat | 480 |
| actaaaaacg taataattaa atattttgct acttcagcag gtcttaatat tttcgaagta | 540 |
| acatgatttt catgagatgg tgcctcatga ttcacagggc ctcgttgtat ttcctgatcc | 600 |
| ttcggtaaat agatcaccat caagaagcca acaataatac tcacaataat taag | 654 |

<210> SEQ ID NO 21
<211> LENGTH: 764
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 21

| | |
|---|---|
| tctaaactta tagacatctt gtttaacctc tttgttagta atccattgac tttgtccatt | 60 |
| atcattcgct tgtttaccat ctaaacttgc agatactttc actgtaattt gtggcagttg | 120 |
| ctttgctttt gctttaaaaa agtcttggta taattgtgat gcacgttcat catcaacgca | 180 |
| ttcaacctca ataccgtgat cccgtaacgt atcatcacca tgtgtatcta acgaattgtc | 240 |
| ttttgttgcg taaactactt tagctatctt acaatcaatt attttgttaa cacagggtgg | 300 |
| tgttgaacca aaatgactac atggctctaa cgtaatataa atcgtcgcac cttcagcatt | 360 |
| ttgttgtgcc atatcaagtg cttgaacctc cgcatgcttg tcacctttc tcaagtgtgc | 420 |
| accaataccg acaatcctac cttctttaac tacaactgcg ccaacgggtg gattaacacc | 480 |
| tgtttgacct tgtaccatat ttgcaagttg aatcgcataa tccataaatt gactcaaatg | 540 |
| atcacctcta taaacaaaaa tcctcacatc atgaattaag atgcaaggag aaaaatttat | 600 |
| cgttaaataa gcctatttgt acacatttt acaaatacgc tacattatct ttgtcgataa | 660 |
| ttaacattct ttctcccatc cagactttaa ctgtcggctc tagaatctca ctagatcagc | 720 |
| cactaatatg aaacatatta gcaggtcgca ggctttattt actg | 764 |

<210> SEQ ID NO 22
<211> LENGTH: 367
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 22

```
ctgatactgt gaaattttg gatctttgta cggtgaaaaa ttgtggcgcc ctcgggtgga      60
agtaggaatc tttggtcgga gacgtcggcc acagtaggaa ttcgttggtg agtgcggtcg     120
aatgtcaagt ttacagacta caatcatgac tataggggaat agaaaaaatt aaaaaatttg    180
ttcatttaat acttcgatgc ctgatgagcg ctaattcatt ggaaacttac aatgctgata     240
atgatcgaaa aataagaccg atgaatcaat gtattgtgtt tagtttcctg aagattgagg     300
ggaaggtgca aaagatactt tgattcgaca tgatgttaat gaagacaata ttgatgtagc     360
atttgtt                                                                367
```

<210> SEQ ID NO 23
<211> LENGTH: 767
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 23

```
ttttactcat gcatgcctat tttcaagtga gtctgagaca taaatcaatg ttctacgctt      60
tacaaagtta tattggcagt ggggccccaa tacagagaaa ttggaatccc aatttcaaca     120
aacaatgcga gttggggcgg tacaacgaaa tgaattttgt gaaatatca tttctgtccc      180 attccctgat gaatatgtgt atttaaaaag gacgttacct acattaaagt aagtcacgtc     240
cgtatgctta tgatttactg tcactgtttt caattcgatt gatagtaaca tttagtccaa     300 aatattttc taaaaaatgt ttatagttat ctttagtgac agctaactt tctgagatgc       360 catccttgtgc ttttgtcaaa gttaaatgat tttcagacat tgtagcacgg ccaaacgatt     420
gtggcattgt aattaataaa tgctgtacaa atattgaatc tggatgcgtt tgattatatt     480
caatattttt atcaaaatct gcaatacatt tagctttaaa ttcagcttca tattttgtat     540
gccaatgatc attttcgaat ttttgaacat agaaaatatc cttgtcttcg ttgttaaaga     600
tagcacgaaa cgtaccactg atgtcagtaa tcggttgtgt atgctctgac gaagtaatag     660
gaatggcgtg tagaggtaag tctccaaagc caacatcagt tacatagaat acatcattta     720
tagaaacaac aagtgaagca tgtgaaccgt tcagactgcg accgcca                   767
```

<210> SEQ ID NO 24
<211> LENGTH: 698
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 24

```
catgaaggaa atattaccca tcaatttcat aaatgctatt gcggcgaata ctgcatgtaa      60
tatagcaatc aataatggta aaccgaagtt gaaagtaatt tttaataata atcccttaag     120
catatctgta tgcgtaaagc ctatgcgttt taatattctg aagttactta gttcatcctc     180
agtttcatcc atttgtttaa tataaataat acatccagct gctactaaaa atgctaatcc     240
```

| | |
|---|---|
| taaaaatgat gtaacaaata ttagaatacc gttagtagca tcgacctctt ttttcatgtc | 300 |
| atcatacgtg attactttgt ctccaaactg ttttgcaatt gcttgagctt tttccttttg | 360 |
| tgatgtttgt ttaatatcat acccataaaa agtatgaaca ttattttgtg ttttcaactg | 420 |
| ctgatacttt tcaggactta cttcgacgac aggtgagttg aagcttagat ttaaaggata | 480 |
| aaccttacct ttgtcttctt gtgtaacacg gaaagtttca ttcttagttc cttttactac | 540 |
| taaatctttg tttaaaagga tattaatcac gttaggcagc gactttgtat ttgtaatgat | 600 |
| ggcattgtta ccagttaact ttgtatttgc acttaaaata gaattcgtgc gacctgaatc | 660 |
| actaccattt tccaaagtaa taacctgatc tttaacat | 698 |

<210> SEQ ID NO 25
<211> LENGTH: 774
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 25

| | |
|---|---|
| agggttatac gatatcacac agcaagcgaa tgctaaggca gctggtattc gtattgctgt | 60 |
| tgccgaaaag gcgggaaagt tgtcggcatg tatttattag aaaacagagg gagttcacat | 120 |
| tccacctcgt tacaaaatgt ttttgctctc gtgcgagaat caaaactgtc tatgaaaatc | 180 |
| gaattcgatt gattgagtgc atactctttt taattattaa catatttccg ttttcccaat | 240 |
| ggaggagacc tttactgaga tacatctttt gctaattctg tcaaaaccaa tagattatgg | 300 |
| tatgcaagtg gcttacctgc gagcgatcag tattgaaaac cactggaaaa catctatctc | 360 |
| atccttcgat ttctgttttc gaccctatta cagttgtaga tacacaggtg tgctatggat | 420 |
| caaagatgaa ggcttgattg ttattttaaa tatgggccag cacgacagtt ccatcttttc | 480 |
| tatatcgaac gaactctaat gttcccattt attgttacaa tgcctcgtaa tcccctcta | 540 |
| ttaagagctg aagattctta ttactaacaa ggcctaaata gatagatgct acggaacact | 600 |
| tctccaaaca acaaaattat tatcttttt tcttcccgga aatgttttcc atgctgactt | 660 |
| cacccccggaa cgactgtcag ctacaccgat tagtgcgacc atacgggtca tcttgcttct | 720 |
| tgctacatga aaaagaaca atcctacaaa taaagattat gtctaggtgc acgt | 774 |

<210> SEQ ID NO 26
<211> LENGTH: 703
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 26

| | |
|---|---|
| gatttcccta atgcagcaaa agatgaacat ggtcgtctac ttgtagccgc agcaatcggt | 60 |
| atttcaaaag acactgatat tcgtgctcaa aaattagtcg aagcaggtgt ggatgtctta | 120 |
| gttatcgata cagcacatgg tcactctaaa ggtgttatcg atcaagtgaa acatattaag | 180 |
| aagacttacc cagaaatcac attagttgca ggtaacgtag caactgcaga agcaacaaag | 240 |
| gatttatttg aagcgggtgc agatattgtt aaagttggta ttggcccagg ttcaatttgt | 300 |
| acgacacgtg ttgtagcagg tgttggtgta ccacaaatta cagcaattta tgattgtgca | 360 |
| actgaagcgc gcaaacatgg taagctatc attgctgatg gtggtattaa attctcagga | 420 |
| gatatcatta agcattagc tgctggtgga catgcggtta tgttaggtag cttattagca | 480 |

| | | |
|---|---|---|
| ggtactgaag aaagtccagg cgcaacagaa attttccaag gtagacaata taaagtatac | 540 | |
| cgcggtatgg gctctttagg tgcgatggaa aaaggttcaa acgaccgtta cttccaagaa | 600 | |
| gacaaagcgc ctaagaaatt tgtacctgaa ggtatcgaag gacgtacagc atataaaggt | 660 | |
| gctttacaag atacaattta ccaattaatg ggcggagtgc gtg | 703 | |

<210> SEQ ID NO 27
<211> LENGTH: 1488
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 27

| | |
|---|---|
| atggctaaga ctcaagcaga aataaataaa cgtttagacg cttatgcaaa aggtacagta | 60 |
| gacagtcctt atagaattaa aaaagctaca agctatgacc catcgtttgg tgtaatggaa | 120 |
| gcaggagcaa ttgacgcaga tggttactat catgcacagt gccaagactt aattactgat | 180 |
| tatgtattat ggttaacaga taataaagtt agaacttggg gtaatgctaa agaccaaatc | 240 |
| aaacaaagtt atggtactgg atttaaaata catgaaaata aaccttctac agtacctaaa | 300 |
| aaaggatgga ttgctgtatt tacatccggt agttatcagc aatggggtca cataggtatt | 360 |
| gtatatgatg gagtaatac ttctacattt actatttag agcaaaactg gaacggttac | 420 |
| gctaataaaa aacctacaaa acgtgtagat aattattacg gattaactca ttttattgag | 480 |
| atacctgtaa aagcaggaac tactgttaaa aaagaaacag ctaagaaaag tgcaagtaaa | 540 |
| acacctgcac ctaaaaagaa agcaacacta aaagtttcta agaaccatat taactataca | 600 |
| atggataaac gtggtaagaa acctgaagga atggtaatac acaacgatgc aggtcgttct | 660 |
| tcagggcaac aatacgagaa ttcattagct aacgcaggtt atgctagata tgctaatggt | 720 |
| attgctcatt actatggctc tgaaggttat gtatgggaag caatagatgc taagaatcaa | 780 |
| attgcttggc acacaggaga tggaacagga gcaaactcag gtaactttag atttgcaggt | 840 |
| attgaagtct gtcaatcaat gagtgctagt gatgctcaat tccttaaaaa cgaacaagca | 900 |
| gtattccaat ttactgcaga gaatttaaa gaatggggtc ttactcctaa tcgtaaaact | 960 |
| gtaagattgc atatggaatt tgttccaaca gcttgtcctc atcgttctat ggttcttcat | 1020 |
| acaggattta atccagtaac acaaggaaga ccatctcaag caataatgaa taaactaaaa | 1080 |
| gattatttca ttaaacaaat taaaaactac atggataaag gaacttcaag ttctacagta | 1140 |
| gttaaagacg gtaaaacaag tagcgcaagt acaccggcaa ctagaccagt aacaggctct | 1200 |
| tggaaaaaga accagtacgg aacttggtac aaaccggaaa atgcaacatt tgttaatggt | 1260 |
| aaccaaccta tagtaactag aataggttct ccattcttaa atgctccagt aggaggtaac | 1320 |
| ttaccggcag gagctacaat tgtatatgac gaagtttgta tccaagcagg tcacatttgg | 1380 |
| ataggttaca atgcttacaa tggtaacaga gtatattgcc ctgttagaac ttgtcaagga | 1440 |
| gttccaccta atcatatacc tgggggttgcc tggggagtat tcaaatag | 1488 |

<210> SEQ ID NO 28
<211> LENGTH: 495
<212> TYPE: PRT
<213> ORGANISM: Artificial Sequence
<220> FEATURE:
<223> OTHER INFORMATION: Description of Artificial Sequence: Note = Synthetic Construct -continued

```
<400> SEQUENCE: 28

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
            20                  25                  30

Asp Pro Ser Phe Gly Val Met Glu Ala Gly Ala Ile Asp Ala Asp Gly
        35                  40                  45

Tyr Tyr His Ala Gln Cys Gln Asp Leu Ile Thr Asp Tyr Val Leu Trp
    50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Gln Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Ser Thr Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415
```

```
Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn His Ile Pro Gly Val Ala Trp Gly Val Phe Lys
                485                 490                 495

<210> SEQ ID NO 29
<211> LENGTH: 17938
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 29
taaatataat cggaaaaagt ttttgtaaat ttacacctcc ccaccgttta aaataaacga      60
ttatacaaat caaaacttat aaattaactt atcatttcta aactaaactt ataaaaaatg     120
ttcacctact ttcccaactt atctaaccta ttacatattc attaattaca aaatatatac     180
atctattgac ttttatccaa aattatgatt tgaaattaaa atctagtttc ttctattaaa     240
tagtagtttt aaattattta aactttttta cgatatttta ttgacaaaac atttaaacat     300
ttgctatact aagtatgtaa tcaaaacaag gaggtaacaa aaatgattaa tgttgataat     360
gcaccatcag aaaaaggtca agcatatact gaaatgttgc aattattcaa taaactgatt     420
caatggaatc cagcatatac gtttgataac gcaattaact tagtatctgc ttgtcaacaa     480
ctattattaa actataacag ttctgttgtt caattcttaa atgatgaact caacaacgaa     540
actaagccag aatctatttt agcttatatt gctggtgacg atgcaatcga acagtggaat     600
atgcacaaag gttttatga aacgtataat gtttacgtat tttagaaagg aatgatataa      660
tgaaagctga tgacattata actttacgtg ttaaaggtta tatattccat tacttagatg     720
aatcaaatga atacattgaa gaatttatac cacttcacga gtatcattta actaaaacac     780
aagcaataga attattaccct aacacatgta cactattatc aactcacgc aaaacgaaaa     840 aaatccaagt atattacaat gatttactac aaatttcaat taaagaggag aaataaaaaa     900
tgacaaacgt aaaagaaatt ttatcaagac accaaaatac aacagcgaga tttgaatttg     960
aggaaaaaga aagagaattt ataaaactat cagaattagt tgaaaaatac ggtattaaaa    1020
aagagtatat cgttagagca ttattcacaa acaaagaatc aaaattcggt gtacagggtg    1080
ttatcgtcac tgacgactat aatgtaaact taccgaacca cttaacagag ttaattaaag    1140
aaatgagatc agacgaggac gttgttaaca ttatcaatgc tggtgaagtg caatttacaa    1200
tttatgaata tgaaaacaaa aaaggtcaaa aaggttactc aatcaacttt ggtcaagtat    1260
cattttaata caatttcata ggggatattt atcccctatt ttatgaggtg ctaaacaatg    1320
gaaaaaatat acactgccgt attattatac aatgtatcaa ttaatgaaac atatgaacat    1380
gaaattgaac aattcgaaaa aataaataaa gttaaggtaa tatatagtta ttttgacgca    1440
aacttttaca aaaaggtgc atataatttt ggtgtaaaat acattaagga gatataaaaa    1500
tgaatattac aacaacatta aacacaaaaa aattaattaa ttatatttta gataatagag    1560
attgttttat gaataaaata acaaaattta catcactaag tggaaaatgt gttgtttttg    1620
```

```
ttagatacgg tgaaatttct attgaatact atgatagtga tacaaaaaac aataatgatt    1680
tatttacttt agacattgac gttgatatta ataaacatgt ctttaattgt cttaaagttt    1740
attatataga acatacagaa gatataaaca taatatataa aaaaggtgta tacatggggt    1800
gtactattga tgatgtatta tcatattttg aaaaaccatt agaaagtgat attactatta    1860
tttaccaagg caaagttatt tatgaatacg ggaaagtaat agaccatgaa taacctacta    1920
gatattatta ttgttttcct tttagcattt ttaattacac ttgtaatact tatgacaatg    1980
tatatacgtg tgtcatttgg tgttttattt actacatttta ttatattcta cattatcttt    2040
ttattggttg tatatgcttt atatggaggt tgataacatt ggtttagaca tacgtctgaa    2100
atggatagat ggaaaaaaga aagagaagct agaaagaaaa gagaagaaaa aaaatataaa    2160
aatgatttta gcggtatcaa tttttaaattt gacgataaag atttacaaga ggcttatatt    2220
gacgcatgga aacatttttc acatttacca catttaccaa aagaaaaaaa tgtatctcat    2280
gcaaacgctg tttcattagt tcgtggtaaa cgacataaaa aattaaatca tatactagaa    2340
atatataacc gtaatgataa taataacaaa aatgcaaaaa tgcataaata tgcattatat    2400
aatttacacg ccgaaaaaaa taaatcttca cttacaaaat atattaaaga aattgataac    2460
ttattttttg aaataggaaa atcagataga ccaaaaacaa caatagatga tatcaatgtt    2520
aggtataact ttttatatta tgcaacattt gaagaataac tttaatactg taaatgacat    2580
tataaactat tacaaggagc aaaaacatgg tgaaacaaaa tcgtttagac atggtaagag    2640
attatcaaaa tgcggtcaat catgtaagga aaaaaatacc agaaaactat aatcaaaatag   2700 aattagttga tgaactcatg aatgatgata tagactatta tatatctatt tcaaaccgtt    2760
ctgacggaaa atcgttcaac tatgtttcat ttttttattta tttagctatt aaacttgata    2820
taaaatttac tttattatca cgtcattata cattacgtga cgcttaccgt gattttattg    2880
aggaaatcat agataaaaac ccactattca aatctaagcg tgtcacttc agaagcgcta    2940 gagattattt agctattatc tatcaagata agaaattgg cgtgattaca gatttgaata    3000
gcgctactga tttaaaatat cattctaact ttttaaaaca ctaccctatt attatatatg    3060
atgaattctt agcgcttgaa gatgactatt taattgatga gtgggacaag ttaaaaacaa    3120
tttatgaatc aatcgaccgt aaccatggta atgttgatta tattggtttt cctaaaatgt    3180
ttttactagg taatgctgtc aacttttcaa gtcctatatt atccaattta aatatttata    3240
atttattaca aaaacataaa atgaatacat caagacttta caaaaacatt ttttagaaa     3300 tgcgtcgaaa cgattacgtc aatgagaggc gtaaacacg tgcgtttaat tcaaatgatg    3360
acgctatgac aactggcgag tttgaattta acgaatataa tttggcagat gataatttaa    3420
gaaatcatat caaccaaaac ggtgattttt tctatattaa aactgacgat aaatatataa    3480
aaattatgta taatgttgat acatttaatg ctaacatcat tgtaatacct tatacaaaac    3540
aatatgagtt ttgcactaaa atcaaagata tcgatgacaa tgttatttat ctaagagaag    3600
atatgtttta taagaaaaac atggaacgat attactacaa tccaagtaat ttacatttg     3660 acaatgctta ttcaaaaaat tacgtggttg ataatgatag atatttatat ttagatatga    3720
ataaaattat aaaatttcat ataaaaaatg aaatgaagaa aaatattaac gaatttgaaa    3780
gaaaagaaaa gatatacgaa gataactata tagaaaatac aaagaagtat ttaatgaaac    3840
aatacggctt ataaaaggtg tgtaagatta tgggattact tgagtgtatg caatatcata    3900
aaaatcaacg taaaatgata ttgtactggg atattgaaac attatcgtac aataaaataa    3960
acggacgcaa taaaccaaca ttatataaaa acgtaacgta ttctgttgcg attggttggt    4020
```

```
ataatggtta cgaaattgat gttgaagtat tccccagttt tgaagccttt tatgatgatt    4080
ttttcaagta tgtttatcgc cgggatacaa tcacaaaatc aaaaacaaat attatcatga    4140
ttgcacataa ctgtaataaa tacgataatc attttttact taaagacacc atgcgttatt    4200
ttgataatat tacacgcgaa aatgtatatt taaaatctgc agaagaaaat gaacatacaa    4260
taaaaattca agaggctact attttagcca aaatcaaaa tgtgatttta gaaaacgtg      4320
ttaaatcttc aatcaattta gatttaacga tgttttaaa tggttttaaa tttaatatca    4380
ttgataactt tatgaaaacc aatacatcaa tagcaacatt aggaaaaaag ctacttgacg    4440
ggggttattt aacagaaaac caacttaaaa cagattttaa ttatacaatt tttgataaag    4500
ataacgatat gtcagatagt gaagcttatg actatgctgt taagtgtttt gataatctta    4560
catctgaaca attaacctac attcataatg acgtgattat attaggtatg tgccatattc    4620
attatagtga cattttttcca aattttgact ataacaaatt aacattctca ctaaatatca    4680
tggaatctta tttgaataat gaatgactc gttttcagtt actcaatcaa tatcaagata    4740
ttaaaatatc ttatacacat tatcattttc atgatatgaa tttttatgac tatataaaat    4800
cattttatcg tggtggttta aatatgtata ataccaaata tcaataaaa cttattgatg     4860
aaccttgttt ttctatagac atcaattcga gttatcctta cgtgatgtat catgagaaaa    4920
ttccaacatg gttatacttt tatgagcatt actcaaaacc aacattaatc cctactttt     4980
tagatgatga taattatttt tcattatata agattgataa agaggtattt aacgatgagg    5040
tattaattaa aatcaaatca cgcgtactac gtcagatgat tgttaaatac tacaataatg    5100
ataacgatta cgttaatatc aatacaaaca cattaagaat gatacaagac attacgggta    5160
ttgattgcac gcatatacgt gttaattcgt ttgttgtata tgaatgtgaa tactttcacg    5220
cacgagatat tatatttcaa aactatttta ttaaaacaca aggtaaatta aagaataaaa    5280
tcaatatgac aacaccttac gactatcaca ttacagatga aattaacgaa cacccctact    5340
caaatgaaga agtatgtta tcaaaagtcg ttttaaatgg tttatatggt ataccgctt      5400
tacgttcaca cttaatttta tttcgtttag atgaaaacaa cgaattgtat aacatcatta    5460
acggatacaa aaacacggaa cgtaaatatt tattctctac atttgtcaca tcacgttcat    5520
tgtataactt attagtacct ttccaatact taacgaaag tgaaattgac gacaatttta    5580
tttattgcga cactgatagt ttgtatatga aatcagttgt aaagccctta ttgaacccca    5640
gtttattcga ccctatatca ttaggcaaat gggatattga aaacgaacag atagataaga    5700
tgtttgtact gaatcataaa aaatatgctt atgaagtgaa tggaaagatt aaaattgcgt    5760
ctgctggtat accgaaaaac gccaaaaata caagcgtcga ttttgaaacc tttgtacgtg    5820
aacaatttt tgacggtgca attatagaaa acaataaaag tatctataat aatcaaggta    5880
cgatatcaat ttatccgtca aaaacagaaa ttgtttgtgg taatgtatat gatgaatatt    5940
ttactgatga acttaatta aaacgtgaat ttatcttaaa agacgctaga gaaaattttg    6000
accatagtca atttgatgat attctttata ttgaaagtga tattggttca ttttcactca    6060
atgacttatt tccatttgaa cgttcagtac ataacaaatc tgatttgcat atattaaaac    6120
aacaacatga tgacatcaaa aaaggcaact gttaaaataa cagtcgcctt ttctttgaga    6180
taacatgaaa aatgtgtacg aaaattgatt atgttttgta ttttattac tagcattact    6240
agcatgtgtt cattatagca taaatctta tgcaatacca ctaaagaata caatattatc    6300
acctgcgttt tctggtacac cgttaatgag tgtatacaat aatacacgtg acggtgcaac    6360
gtatggtggt acattatagt ttgcgactaa gaatgaacca tcgtcaaaca cagcaacaac    6420
```

```
tacacccgtg tgaccgatac catatatgct tgcttgtaag tatggcggtt tactagagaa     6480
gccgtaacca acggtaggaa tatgtgttgt tttagcccct aattttttat aaacatacca     6540
cacacgttga ccgtttgtta cttgtccatc atcagttggt tgtcttttc catgtaattg      6600 tgacatatac gcccatgtta attctgtaca ctgaccagca ttaccagttt gagggaatat     6660 gttaccggt  ttgtataaat attctttttt gaataaaggt acaccaattg ctttttata      6720 tttttctggt aattggtcat acgtccagtt accacctatc acgaccac ttttccgtt        6780 tggtttcaca gatttacctc taatcgcatt atgctcacca tcgtcatcag tagggtttga    6840
acttccaccg tcatctattt gcacactatc aatgagcttt tttaatgagt cgagtagtcc    6900
aatcgtcatt ttaatatgat acgtgttgtt aaatgttttt tgtagtgtaa aataatcatt    6960
actaaaaaat ttatcactac caatactatg cacgtcccat tgtaatgcgt cttgaacttt    7020
ttttaataat tcttgcatgg cttgttttgc taaagcgagc agtgaactac cactgtcacc    7080
actactacca ctgtcagacg aatcactagg tgaaccacct ttaccgtcta atttaccacc    7140
ccatgctaaa atagtatttg caccgtctaa aaaaggatta ccatagttt  gtactttatt    7200 atatgacgct tcaaaccta  ggggataata tgccgcccaa gtagctgcag ccgttaatgg    7260
gatataagca cgtccaaccg taccagcttt catgttttta gcaaaatctg cattacctt     7320 tctttgtacg ttttgaggta caaagtgaac gatgttacct gcgtcatacc aagacggttg    7380
tcctgcttgt tttgattgtg atacaagctt tctagctaca aatttagcgt ctgttaaata    7440
atcgccttgt gcagaagtat gatttaacca acctaaacct gcactgtatc cttcgttttt    7500
ttcatataca gcaattagcg taggtgaaac tcctatcgat ttaactgcat ttagaacttg    7560
tctgatttta cttcattac  cacctaacca aacattaaaa cgtccataac ctttacttt    7620 aggcactaac tggtctatcg ttaatccaaa gtcatcatta atataagaat gtgtaaattt    7680
atctatcttc tcttggtcgt tcatctttat cactcttttc agaatcgttt ttaattactc    7740
ttaatttatc tttaatttgt tctggcacta atacatccat ctctgcacaa ttttctacaa    7800
tagataaacc ctcattagca atataataga aaatcgtaat cataagtaga ccacctttta    7860
attgtaaaat ttggtcaatg atatttgcta gaataataat acagaatatg agtaattttt    7920
tagcgaaacc tctcattgat tttttgacc  atagattatt attttttaatg gcttttgaaa   7980 tacctgtaat aatatcaaca acattaata  taaataaaaa atatagtaat tttaaatctc    8040
ctgcatatat aaacatgtga aacacttctg tatctgtaaa cctgaatttt acttcattca    8100
tttttatacc ccctctctaa atttattatt taatggattt tgtaacatag ggttacctga    8160
accatcatta tgccaaaatc tcacaccaga ttccaaaata gcttttaatt gttccattaa    8220
catagggtca atgtcacgta ttgtatacgt acctgtacat tttaaatagt tgcatatagt    8280
catactgtta attggttcaa taaatgtatt atagtcattt acttcaaaac caaacaacat    8340
ataatatttt tgtaaaaatg taatttcttt aggtgacggt acactaattt tcattgttaa    8400
accgttaatg ctatttgcga tttggaaagc gttccccatt tctgactctg tcactgatgg    8460
tggttgtaag gctaaatctt tatattctgc ttgttgttgt ttgtagaaat tatattcttc    8520
attaaactta ccaaataaag cagttggact taaattactt gctacactta cagcgtcata    8580
aaaacgtgat tttgggtcac tgccattaa  tacattatct atacgacttg tgattaattg    8640
actttctgca ttacgctgtc tattggcttg ttgtgattgc cctaaaatac cgttattgat    8700
taaaattggt acttgtgcaa aactattaaa tgttatattt gtatttaaga atgaacctgt    8760
atcaattaat atatctttat tttttgcaag tatcggtcta tcattttcag cactgttata    8820
```

```
atctactgga taaactcgca cttcattatg ataaccaatg atggattttg tacgtaactt   8880
aacacctgtt ttttgtgaaa tcttaccagc gtctagtaac atagtattac cattccagtc   8940
ataaaaatca atcgtcatgt actcattacg tatcatatgg tcgcactcgt ctttttttaga  9000
caacatcatc tcttgaagct ttgtgaaact taatgataaa tcgtttaaac tccattcttt   9060
tgattttcca ccttgtttta acgtctttaa tccagtaatt ttttcacttg tcttaacgtc   9120
ctctaaatct tttgtattaa tagaatcttt aggtaacatt tgaaccttt gaaagttttg    9180
tgtaatccat ggataggcac tcattttatc cataaagtta ataaagtcac catattccat   9240
aacgtataag ttgactggtg atgtgatatt gtcatatatt gtacctttag acgtatctaa   9300
gtttggctct tttttagtac caaatttctt tgataaatca gcacttgact ggaataacac   9360
taaattttcc aaaaactgtt gcatttggtt atacacatag tttttatttg atacttttaa   9420
cacatcatca ttgttacgta acattggtaa catatagtta tacgtgcgtt ttgataagtg   9480
ttgacgttca atattaacgt ttgagagttg ttctaataca ttaccttgtg tatacgtcat   9540
aatagtatca atcacaaaat atattttaac cacaacatca ttcacatatt cgatttgatt   9600
cacaaacgca taataacgtc tgtcctcaaa atctgataaa aacgtcatgt agttaatccc   9660
ttgtgcgtca tgccactgca tatcaacatt gatttccatt ctatcacgta taaaattata   9720
cggttgtttg gaatagtcta atgatttaaa atgacgtcca tttaaaaaat aatcatcacg   9780
ttcttgatta ctattaaaat gaatcgtatt ttgataatca gtaaacggtg tgttatagaa   9840
aaatttaaaa tttgttaatt ttctcatttt tacctccata aaaaatagtc gtataaatta   9900
tttatacgac tattataaca tttttattca atgatttgtg tatctattgc aaaacttttta  9960
ttaccatttg aaagctcact atcactataa tttgatgtaa caaaatgtaa ttcattatta   10020
aagtttaaat ataatcttgt attaatcatt ttcgaatcaa tcgcacattg tgtgtagtga   10080
tgtgtagatt ttaagtttgc gttaatcgta cctaatttaa tatcaccgtt tttcttaatg   10140
cctttttaata ccccttttaa ttgtatggtt ttaacaccat taattgttaa aatacgatat  10200
tgcggtgcag gatatccaac gttgctatca cttgcaataa taccactttc taatgtaata   10260
tcttgccacc ctgtatcatt cacagttgtt ttattttcat taattgtatt taaaatttct   10320
attttatcat tagttattat agcagttaaa ttgttaatac tttgtgtatt attacctaca   10380
ctttcttttg tagctataat atcttgttta tttttttcaa tatcttcttc atttttttgtg  10440
tttttatcat ctaatatatg aattgcagat tcatgattac ttagtttatt tgtatgttct   10500
gattgaacat ctgataaatt ttttatttt ttatcttgtt gcacattatc ttctttaata    10560
ttaataatgt ctgtagcgtt ttgagaaata ttatttttat ttgtagcgat atcatttta    10620
tttttattaa tgtcttttgt gttcgtatta attttactta ataattcatc tttaaaggtt   10680
aacttataat aatcctcatc acgtcttata taaatgttac cgtcctttgt agtaattaag   10740
tcatttgctt ctactaaatt atcatttaat ttatctacag agtcaatgtt gcgcaaactt   10800
ccttaaaatc caacaaccat tggttaaacc ttttatttta atgttttcca actaattcaa   10860
agaaaaattc tattttatca ttagttttta tagcagttaa attgttaata ctttgtgtat   10920
tattacctac actttctttt gtagctataa atcttgtttt attttttttca atatcttctt  10980
cattttttgt gttttttatca tctaatatat gaattgcaga ttcatgatta cttagtttat  11040
ttgtatgttc tgattgaaca tctgataaat ttttatttt tttatcttgt tgcacattat    11100
cttcttttaat attaataatg tctgtagcgt tttgagaaat attattttta tttgtagcga   11160
tatcatttttt attttttattt atgtcttttg tgttcgtatt aatttttactt aatattcat   11220
```

```
ctttaaaggt taacttataa taatcctcat cacgtcttat ataaatgtta ccgtcctttg    11280
tagtaattaa gtcatttgct tctactaaat tatcatttaa tttatctaca gagtcaatgt    11340
tgcgcaaact tcttacaatt ctatcagcca ttgtttacac ctcttattta tatcgtttcc    11400
aactaaattc aaagaaaaat cctaaaatac ccattatgag aacacccccc aaggtacacc    11460
aatactatat gcattacctg ttttttccgtt ccattgtcta actggtaaat aataacgagt    11520
tccttgccag ttataaccaa tccaaactaa cccatctgat aaacaaactt cgtcatatgg    11580
tgtatagccg tttggttgga accaatagcc attaggttca cttaatttag gactacagac    11640
acgtgcaaat attggtaaaa aaccacatgt aaatgttgcc ttttcgtttc tataatatgt    11700
gccgtattgg ttttgtttcc aattattagt tagttgaata ttttgttcta atactttact    11760
ttcactgttt gagaattttg ggcgaataaa atgtgtcaca ccgtcataat aatgtgttct    11820
aattgttgct ttttcccaac catcatatcc accattcaac cagttttgtt ctaaacatgt    11880
ataataatca agatttccac ttgttacaca ttggatatgt ccatattgag aatttgtgta    11940
tactgcaaca tcacctaatt gaggtttaaa gctcgatgta ttttcataca ccgttgctaa    12000
acctttaaag tcattattaa ttgcgtcttt agcattaccc cacatacgca ctttaccgtc    12060
agtaatataa tagatataag caacagctaa gtccatacat tgaaaaccat atgcaccatc    12120
aaagtcaaca ccaacacctt catgtttata tatccaatct ttagcttgtt gttgtgattt    12180
catttataac actcctatttt tttatgtttt gctacccatt catattcacg atgttttgta    12240
tcagcgttca cattactgaa aaactcttta tattctgata tgttagcttc taatgtttgt    12300
ctcacttctc caactgcgtt accacttgac acacgtaacc atgcaccaac acgttttatt    12360
tcttccggtg cgtctttgaa taattccatt tggttgcctg taatataata ttctccgggt    12420
gttgtaacgt aagctatcca attattatat ttacttgctt ctaaatattc ttgatatggt    12480
gcgtctgttt tgattgttgt ccataaacca taatcccatt ttaacgtgaa tacatctagc    12540
gtcataccac gcataacttt taccatttta cgaccagttg aaaaacgtgt taattcttga    12600
acagtaccta atgtttgtgt tgtagggtat acattaatga aacaaccagc gtcaataatt    12660 ttttttacttc catttgtagg catgttttta agcttttctg ccgtactacc gtcaatataa    12720
taaaatccag cttgcgttaa gtcatttaag tcgtcgatat ggtcaggtat agataatgca    12780
cgaccgtcat cttttgttaa tttataattt tgagaacctc ttgcacgtaa tgcttcaaaa    12840
tgttcatatt ctccaagttg gaagaaaccg tataagttat ggaatcgttt accaccaccg    12900
ccattagtca ttgcaagtaa taacgattta cgttttgttt ttgggtttgt ataaatacaa    12960 atacccctcag gctctttaaa attatcacgt gggaagttaa ttccgtcttg gtaagataac    13020
ttaaacgggt aatcgtataa cttttgacca gttgttaatg aatctttgcc aatttgcaca    13080
tgtgaattaa ctgaactgtt accacttaac cagtacaaat catcaccatc aacagcaata    13140
ccttgcatcc aacgtgcatc gttatttttct gaattatcaa ttgtcatttc tttttctaca    13200
ttatcaatat gattttttaac atcagctctt gaacgtacct gtatcgtacc atcaccgaaa    13260
cgtaatacga gtttgtcatt tgcttcatca attaacggtg taaaagaatg tttgtttaaa    13320
agtgactgtg gtgtataatc tgttaaccct ttggcttctt ctaaatctaa tacatagtta    13380
tctttatatg ctacttgcaa cagttttgca acaccatcgt gatgtaacca tatttttcatt    13440 tccccgtttg attgtctttc taatccgatt gttgtaccgt gaccaccttg tacaatacgc    13500
atactagaaa ttaaatcacc actaggcgtt aattttattaa tccaaaatcc ctcaggtgtt    13560
tgtgagtcgg attgtgttga gtacatttga ttcgtttctt tatcaatatt aatagattgg    13620
```

```
ttcacagcgt tacgaatacc cccaaagccc attacaaact taggttcaag ctcatttaat    13680
tcgaacccat taacaaaacg gttaatgtct ttaattaagt ctttaacttc tgctttaaaa    13740
tcattcattt gtttcatttc agcaacttta aataatgcaa atgcagatgt aagaccggca    13800
ctatatttag taaattcatc atgaataatg ttatctatcg taccatcatt taaccaacct    13860
ctaaataatt ctttagcttg gtctgggaat gctttcatta agtcgtccca atttttgaaa    13920
cgttttttta actcatcgtc atagtcccaa atacgatgtg ctaatacttc aatgagcttt    13980
gataatcttg aaatataatc ataatatgat tttgaattgg tattataatc tgctctatca    14040
tcgtaaaacg gtgtataacg ttctctcgtt ttatatattt cgtctaaaaa tggacgaatg    14100
tcgtcaaaat atttaaaatc gttttcatta tatgccataa ttttccacct ttaccaaatt    14160
tgtaaaaaac attttttat caaattcatt taaaattttc tttcttaaat cgtatacttt     14220
atcaatatta tcaattaaat actgttttga aaattgtgtg cctttcgcat tacctttttg    14280
attttgatta cgttttacgt tttgattact ttcgttactt gatttattca cagttttacc    14340
gttatcaatc gtgttattgt ctgcaaattt taacgttgtt ttatctacat caatgttaac    14400
ctcgctttgt ggtaatgaca cataagcatt tctgttcgct gtcataccag ttgaattgtc    14460
taaagatgta gcattttgat ttgatgtttc atctgtgttg tttgttgtat cttcattatg    14520
ttctgtaaaa ccttgtgatt gtagatattt ttcaacttca cttgatgaat aaacaacatt    14580
caaataatcc tcatgtgtga tacatacagt aatcacttgc ataccaaatg cctcaactgt    14640
ttgtctgtta atctctctat ctaaaaaatg aatcgtaaat gattttttaa aaagtaagtc    14700
tgataaatct tctttcaatg aaaaaccttt aaatacttt tcattaacga tagctaaaac    14760
atctttatcg aatttcaaca ttttttgcat aaattgaaaa tcatcatcat aaaacgttaa    14820
tttattatca tttacaaatt cattgaaacc ttttttaata agctcagatt taataaaatc    14880
gtataaagtc attgtatatc tagccattta aatcactact ttcatctttt aaagtgtgt     14940 caaccattga tatttagac gttgtttcat catcgtaata cggttaata tctaaaccat      15000 agcgtttaga taaaaacgtg attggttcac gacctttaa ataaatatta ctatttgatg     15060
ttgtaaaacc acgattactt ttagcttctt catctgatac accactttct ttatcaacag    15120
ctaaagagtt aatacctaaa tagttactta attcactaat cttattttga tactctcttt    15180
tcatctcagt taaagcagga atcacactat tacttgttaa atcaataatg tcatcttctg    15240
cattaaacat aggtgacatt ttaacaaatg gtgcaccgtt atatatttct gatacaagtt    15300
gattaattga ctcgtcatta atttctgatt taaatacctt gctaaatttc gcttgcataa    15360
tcaatgaaaa tcgagataaa acaacttcag ctaattcatc ggtatagtgt tcaatgattt    15420
caatatcact attatactgt ataggtttat tttgcataac aacaaagtta ccactcatac    15480
aattatcgta tagcttatga atttgtagac actcatcagg aattaaatag tcaggtacaa    15540
taaaataaat atcttctttt gttaatcgtt tttgaaattg gaaattaaag tttgatgaaa    15600
aatttggtgc ttgattaaaa taggtattat ttacataacc aagtatcata atttgtttat    15660
ttctagcttc accaaccact acattaatat tttgccttaa tgcagactct aactgtataa    15720
aatctatacc aaccgtatca cgattggtat agtttataag tagggtaaa aattccaaat    15780 aacgattaaa cataagacgt ttaaatctgt tgcgatgttc aacaactctt ttgttgattt    15840
cttttgataa ttcaacgttt aaacctcttt tatcgttgtt catatttacg ctccttttat    15900
tctgttgctt cttcctctag ttttggtgtt acatcttggt cagtaattaa tattttatta    15960
aagaatggac taatagcctt gaatgaataa taatgaatcc agtgtgtgac ctcatcaaat    16020
```

```
tcaccattat agaatggttg ttttaacata cctttggtat aacgtttgta tttaattgca   16080
ttaatatcta aaataaatgc gtataaatct gattttggtt taatttcttc aatgttacca   16140
gtaaactctt taagtttaga aacatcataa gtaaatactg caccaactgg aattgtgtca   16200
ccaatttgcg actgataatc accgtaagca cgtaagaaat caattgtctc ttgattttgt   16260
aatttaaatt cttttgttac tttaaacaca ccacctaaat catcaaaact tataacatgg   16320
tctgtaaaat caataccagc gatttggaat gtgttagcaa tttttgtatc taataggtaa   16380
gattttaaag aatctgttgt taaaataaca atatctttta acttagatac agttgtatat   16440
tgaccaattg caccaccaga agcacggtga acttcattgt atttagcgct gttgttttgt   16500
aagtttaaaa ttgcttcaaa tactttgctt gctaaatctt cttttgatgt tgttttacgt   16560
acgtttgact ctgataattg atttaatgag taatcaacta acattgctcg catttctttt   16620
tcttctaata cattaatatc agaaattttc tttttatata cacctaatgc gtaatttgtt   16680
gcgtctgcta atgtttggaa attgaaacgt gtatcattat tgtttaatgt gaattttgt    16740 ttcttcacaa taccactacc ataaactta gtagccatac gtggataatt acgtttcaac    16800
attaattcct cattttttga taaatccata ttaattggta ctgtatccat aatgacatat   16860
tcttcactat attgaccaat aaagtcttgt tctttagcta accaattaaa acggttacct   16920
aaagcaatat caattaataa tgtctcgtta atcttaggga ataaatattt atttacaaat   16980
gtttcaaaca ttgtattatt gttatcccat ttatcaccaa atgtccaaga ttttgaataa   17040
tcatggttaa aatcttgtaa tgccgacttt gcagatttg ctactaaaag agctgtttcg    17100
ttttttgtac ttgctggtgc cataatttat tattcctcct ctacgtctcc gctaaaagtt   17160
tgttttgaaa gtgaatggat ttgtacaccg tactcatctt cacttttgtt tacatctatt   17220
gacatatttt catttaattc agtacgttta tttaaacgtg aatcttcata tgatgtcccc   17280
atcatagaac gcatgttatt gccttcatac atattatttt cctcctaatc taaatctaac   17340
ttgtcaacta attcttcatc tgaatagtct ttatcttctt tgtcagcatt tgttacatct   17400
ggttgtgttt gttgtggttg ttgaatttgt gatgataaaa aagtagtcat tgttgctct    17460 aatgatgtaa tacgttgttc taatataaca gggtcgaatt ttgaactatc ttcatctgtt   17520
atagtaggtt ctaatttatt cttatttct tcttcaattg tttctactgt tttatcttca    17580
gtaggttctt cagttggttc ttcagttggt tcttcagttg gttctttgtc gtctggtttt   17640
acgatttcct caaattctgt cattgtgaca cctccaaaat attttataac taattatatc   17700
atagaatatt taaataagta aattaaattt attaaaaagc gtgaacatag ttttcaataa   17760
aagtaaatag atgtatatat tttgtaatta atgaatatgt aataggttag ataagttgga   17820
aaagtaggtg aacatttttt ataagtttag tttagaaatg ataagttaat ttataagttt   17880
tgatttgtat aatcgtttat tttaaacggt ggggaggtgt aaatttacaa aaacttttt   17938
```

<210> SEQ ID NO 30
<211> LENGTH: 750
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 30

```
atgaaatcac aacaacaagc taaagattgg atatataaac atgaaggtgt tggtgttgac     60
tttgatggtg catatggttt tcaatgtatg gactagctg ttgcttatat ctattatatt     120
actgacggta aagtgcgtat gtggggtaat gctaaagacg caattaataa tgactttaaa    180
```

-continued

```
ggtttagcaa cggtgtatga aaatacatcg agctttaaac ctcaattagg tgatgttgca    240
gtatacacaa attctcaata tggacatatc caatgtgtaa caagtggaaa tcttgattat    300
tatacatgtt tagaacaaaa ctggttgaat ggtggatatg atggttggga aaaagcaaca    360
attagaacac attattatga cggtgtgaca cattttattc gcccaaaatt ctcaaacagt    420
gaaagtaaag tattagaaca aaatattcaa ctaactaata attggaaaca aaaccaatac    480
ggcacatatt atagaaacga aaaggcaaca tttacatgtg ttttttttacc aatatttgca    540
cgtgtctgta gtcctaaatt aagtgaacct aatggctatt ggttccaacc aaacggctat    600
acaccatatg acgaagtttg tttatcagat gggttagttt ggattggtta taactggcaa    660
ggaactcgtt attatttacc agttagacaa tggaacggaa aaacaggtaa tgcatatagt    720
attggtgtac cttgggggggt gttctcataa                                    750
```

<210> SEQ ID NO 31
<211> LENGTH: 249
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 31

```
Met Lys Ser Gln Gln Gln Ala Lys Asp Trp Ile Tyr Lys His Glu Gly
1               5                   10                  15

Val Gly Val Asp Phe Asp Gly Ala Tyr Gly Phe Gln Cys Met Asp Leu
            20                  25                  30

Ala Val Ala Tyr Ile Tyr Tyr Ile Thr Asp Gly Lys Val Arg Met Trp
        35                  40                  45

Gly Asn Ala Lys Asp Ala Ile Asn Asn Asp Phe Lys Gly Leu Ala Thr
    50                  55                  60

Val Tyr Glu Asn Thr Ser Ser Phe Lys Pro Gln Leu Gly Asp Val Ala
65                  70                  75                  80

Val Tyr Thr Asn Ser Gln Tyr Gly His Ile Gln Cys Val Thr Ser Gly
                85                  90                  95

Asn Leu Asp Tyr Tyr Thr Cys Leu Glu Gln Asn Trp Leu Asn Gly Gly
            100                 105                 110

Tyr Asp Gly Trp Glu Lys Ala Thr Ile Arg Thr His Tyr Tyr Asp Gly
        115                 120                 125

Val Thr His Phe Ile Arg Pro Lys Phe Ser Asn Ser Glu Ser Lys Val
    130                 135                 140

Leu Glu Gln Asn Ile Gln Leu Thr Asn Asn Trp Lys Gln Asn Gln Tyr
145                 150                 155                 160

Gly Thr Tyr Tyr Arg Asn Glu Lys Ala Thr Phe Thr Cys Gly Phe Leu
                165                 170                 175

Pro Ile Phe Ala Arg Val Cys Ser Pro Lys Leu Ser Glu Pro Asn Gly
            180                 185                 190

Tyr Trp Phe Gln Pro Asn Gly Tyr Thr Pro Tyr Asp Glu Val Cys Leu
        195                 200                 205

Ser Asp Gly Leu Val Trp Ile Gly Tyr Asn Trp Gln Gly Thr Arg Tyr
    210                 215                 220

Tyr Leu Pro Val Arg Gln Trp Asn Gly Lys Thr Gly Asn Ala Tyr Ser
225                 230                 235                 240

Ile Gly Val Pro Trp Gly Val Phe Ser
                245
```

BACTERIOPHAGE OR LYTIC PROTEIN DERIVED FROM THE BACTERIOPHAGE WHICH EFFECTIVE FOR THE TREATMENT OF *STAPHYLOCOCCUS AUREUS* BIOFILM

CROSS-REFERENCE TO RELATED APPLICATIONS

The present application is a National Phase Application of International Application No. PCT/KR2008/005434 filed Sep. 12, 2008, which claims priority to Korean Patent Application No. 10-2007-0092859 filed Sep. 13, 2007, which applications are incorporated herein fully by this reference.

TECHNICAL FIELD

The present invention relates to a use of *bacteriophage* or lytic protein derived from the *bacteriophage* for the removal (destroy) of biofilm formed by *Staphylococcus aureus*. The present invention also relates to a use of *bacteriophage* or lytic protein derived therefrom which is effective in eliminating biofilm formed by *Staphylococcus aureus* for the treatment of disease caused by biofilm-forming *Staphylococcus aureus*. Therefore, the present invention provides a composition for the removal of biofilm formed by *Staphylococcus aureus* containing *bacteriophage* or lytic protein derived therefrom as an active ingredient and a pharmaceutical composition containing *bacteriophage* or lytic protein derived therefrom as well as conventional antibiotics to improve the antibacterial activity of the conventional antibiotics. The present invention provides a disinfectant, a medical cleaner and an environmental purifier for the purpose of removing biofilm formed by *Staphylococcus aureus* and also provides a therapeutic agent and antibacterial agent for treating diseases caused by biofilm-associated *Staphylococcus aureus* infection.

BACKGROUND ART

In a region infected with bacteria, a mucose structured community of bacterial cells enclosed in polymer matrix is found. This complex aggregation of bacterial cells is called biofilm or biological film (J Bacteriol 176: 2137-2142, 1994). In the biofilm, a bacterial colony is enveloped by extracellular matrix (mucosal surface) comprising polymer matrix (composed of polysaccharides and polypeptides). That is, biofilm is a complex composed of a solid biological surface. the bacterial colony, and a non-biological surface, the extracellular matrix. Therefore, in this invention, biofilm indicates the entire structure composed of such extracellular matrix and bacterial colony therein. Biofilm is the concept first proposed in the late 1970 by Professor Costerton, Chief of The Center for Biofilm Engineering, Montana State University, USA, which indicates the environment where many bacteria survive covered by extracellular matrix made of viscous materials secreted by bacteria (the bacteria adhered on a solid surface secrete viscous materials such as polysaccharides, etc). Biofilm is found everywhere in nature. Mucous slime found in rock or pond is one example. Biofilm is a small city of bacteria where bacteria communicate and defense themselves from outside world. So, biofilm provides an environment for bacteria to survive under diverse environmental stress including antibiotics.

Biofilm is frequently observed not only in nature but also in relation to infectious disease. It can be formed in organs of human and generated as plaques on teeth and can be generated on medical devices for transplantation or industrial equipments. Therefore, biofilm has been a major concern of researchers who study earache in middle ear and pneumonia accompanied with periodontal disease or cystic fibrosis. According to the report made by NIH, USA in 2002, maximum 80% of total bacterial infection was spread through biofilm.

Even antibiotics effective on planktonic bacteria lose their effect once bacteria form biofilm (Trends Microbiol 9: 34-39, 2001). Once bacteria form biofilm, an antibody cannot invade through the extracellular matrix of biofilm, resulting in disablement of host immune system. One of the best-known of the biofilm-specific properties is the development of antibiotics resistance that can be up to 1.000-fold greater than planktonic cells (Antimicrob Agents Chemother 47: 3407-3414, 2003). The mechanism of increase of resistance against antibiotics by biofilm has not been disclosed but can be outlined by the following three reasons. The first reason is "ecological change of microorganisms". Once biofilm is formed, adhesion among bacteria becomes strong, so that bacterial colony is not apt to be spread, resulting in the decrease of proliferation. Then, bacteria begin to lose dependence on interaction with environment and accordingly metabolism of bacteria becomes slow and sensitivity against antibiotics decreases.

The second reason is physical properties of "extracellular matrix composed of viscous polysaccharides". Viscous polysaccharides forming the extracellular matrix have electric property being apt to bind antibiotics. The binding of viscous polysaccharides to antibiotics interrupts the spread of antibiotics. That is, antibiotics cannot be delivered to target bacteria, so that the antibiotics cannot take an effect. The third reason is the "production of an inhibitor", which is presumably involved in the general antibiotic-resistance acquirement mechanism. The most representative inhibitor inhibiting the effect of antibiotics is β-lactamases produced by *Pseudomonas*. Once biofilm is formed, bacteria residing therein but not having resistance start acquiring the resistance related genes by horizontal gene transfer and as a result these bacteria turn into resistant bacteria. Once biofilm is generated on infected area, it can be judged the area has become antibiotic-resistant condition. Therefore, once biofilm is generated, it is very difficult to treat infectious disease by using general antibiotics.

Thus, formation of biofilm indicates chronic bacterial infection. As described hereinbefore, sensitivity of bacteria to antibiotics becomes weak, suggesting that normal doses of antibiotics are not effective. To overcome such low sensitivity, antibiotics are over-used, only resulting in production of antibiotic resistant bacteria. That is, bacteria infection, particularly when biofilm is already generated, treatment with antibiotics is not effective any more.

To prevent antibiotics from being disabled by biofilm, a novel antibiotic capable of destroying biofilm is required or a method for co-treatment of a conventional antibiotic and a specific component capable of destroying the extracellular matrix of biofilm has to be developed in order for the conventional antibiotics to be effectively functioning.

*Staphylococcus aureus* is Gram-positive bacteria, which is a pathogenic microorganism causing purulence, abscess, various pyogenic infection, and sepsis. This is a very dangerous pathogen demonstrating the highest resistance against methicillin (73% at average, which is the top level of resistance world widely), according to the investigation in Korea. That means *Staphylococcus aureus* that is not killed by methicillin takes 73% by its total population, indicating that *Staphylococcus aureus* is a very dangerous pathogen. Many strains of *Staphylococcus aureus* are able to form biofilm.

Once biofilm is generated, drug delivery is impossible, resulting in chronic infection. That is, biofilm formation causes chronic infection (FEMS Microbiology Letters 252: 89-96, 2005). The treatment of biofilm-associated disease caused by *Staphylococcus aureus* is especially difficult, compared with other bacteria infection treatments dealing with biofilms generated by other pathogens. Even if a drug is administered for treating disease, delivery of the drug is difficult because of biofilm. Even if the drug is delivered, the treatment effect on highly resistant *Staphylococcus aureus* is not so great by the conventional antibiotics based treatment. Therefore, to treat biofilm of *Staphylococcus aureus*, a novel approach with a novel material is necessary.

Various attempts have been made so far to treat biofilm generated by *Staphylococcus aureus*. However, the results were not successful. The only effective attempt was using lysostaphin, precisely it was reported that lysostaphin could be useful for removing biofilm generated by *Staphylococcus aureus* (Antimicrob Agents Chemother 47: 3407-3414, 2003). Lysostaphin is an antibacterial enzyme produced by *staphyolococcus* that is able to destroy cell wall of *staphyolococcus*. This enzyme is glycylglycine endopeptidase that specifically digests pentaglycine cross bridges found in peptidoglycanstructure of staphyolococcus. So, lysostaphin is expected as an extremely potent anti-staphyolococcal agent. Even if lysostaphin has an excellent anti-bacterial effect, it is not perfect. There are still many *staphyolococcuses* which are not sensitive to lysostaphin (lysostaphin-resistant strains) (J Clin Microbiol 11: 724-727, 1980; Antimicrob Agents Chemother 47: 3407-3414, 2003). Since lysostaphin sensitivity is different among *staphyolococcuses*, it cannot be effective in every *staphyolococcus*. Moreover, lysostaphin resistant strains are being generated. Such lysostaphin-resistant strains are called lysostaphin-resistant *Staphylococcus aureus* variants (Antimicrob Agents Chemother 51: 475-482, 2007). The mechanism of acquiring resistance against lysostaphin has not been explained, yet. But, there was a report concerning the mechanism saying as follows. When femA gene is mutated and thus nonfunctional FemA protein is expressed, monoglycine cross bridges are generated in peptidoglycan structure, which makes lysostaphin powerless (J Bacteriol 188: 6288-6297, 2006). To overcome the above problem of using lysostaphin, studies have been actively undergoing to establish a method to use lysostaphin together with another enzyme such as lysozyme or antibiotics such as methicillin, oxacillin and vancomycin for better effect (Antimicrob Agents Chemother 21: 631-535, 1982; J Antimicrob Chemother 59: 759-762, 2007; Folia Microbiol (Praha) 51: 381-386, 2006). In spite of co-treatment, if *Staphylococcus aureus* has a low sensitivity against lysostaphin or resistance, removal of biofilm is still impossible. Therefore, a novel substance is required to overcome the disadvantages of lysostaphin treatment. The novel substance might be administered independently or co-administered with the conventional antibiotics. It will be more preferred if the novel substance can be functioning by different mechanism from lysostaphin or the conventional antibiotics.

The new approach drawing our attention these clays to be able to complement the conventional art is to use *bacteriophage*. *Bacteriophage* is a kind of virus-like agent that infects bacteria and is generally called 'phage' in short. *Bacteriophage* is a simple structured organism in which a genetic material composed of nucleic acid is covered with a protein envelope. The nucleic acid is single-stranded or double-stranded DNA or RNA. *Bacteriophage* was first found by Twort, an English bacteriologist, in 1915 during his study on the phenomenon of melting down of *micrococcus* colonies as being transparent. In 1917, d'Herelle, a French bacteriologist, discovered that there was something decomposing *Shigella disentriae* in a filtrate of a dysentery patient's feces and later through his further research he isolated *bacteriophage* independently and named it as *bacteriophage*. The term *bacteriophage* means 'eating bacteria'. *Bacteriophage* needs a host for its survival and every bacterium has its specific *bacteriophage*. *Bacteriophage* invades into a host and is multiplicated therein. Then, *bacteriophage* expresses a group of enzymes necessary for decomposing cell wall of a host bacterium. These enzymes destroy cell wall of a host bacterium by attacking peptidoglycan layer involved in rigidity and mechanical strength of cell wall. Such bacteriolytic protein of *bacteriophage* plays a role in destroying cell wall of a host bacterium to pave the way for *bacteriophage* to get out of the host. Such bacteriolytic protein of *bacteriophage* is generally called lysin.

Antibiotics (antibacterial agents) are still major part of the treatment of infectious disease by bacteria. However, since 1980s, excessive use of antibiotics has generated many antibiotic resistant strains and since year 2000, multidrug-resistant strains have been frequently reported. With the recognition of problems of using the conventional antibiotics, studies have been focused on *bacteriophage* as a highly potent alternative for the conventional antibiotics in many advanced countries. *Bacteriophage* is not only effective in treatment of antibiotic-resistant strain but also effective in treatment of patients with allergy to antibiotics. It was once reported that lysin was used to kill *Bacillus anthracis* usable as a biochemical weapon for bioterror (Nature 418: 884-889, 2002). Since then, studies have been actively undergoing to understand lysin having a specific bactericidal activity and its functions.

As an alternative for the conventional antibiotics, *bacteriophage* and lytic protein derived therefrom also draw our attention as a biofilm remover. There is a description on the use of *bacteriophage* itself in relation to biofilm (International Publication Number WO 2006/063176 A2; WO 2004/062677 A1). However, *bacteriophage* has a narrow window of effect, suggesting that one *bacteriophage* cannot be effective in whole bacteria of one species. So, to secure the effective treatment, diverse *bacteriophages* are necessary. And if necessary, combination of different *bacteriophages* might be required. The *bacteriophage* mixture containing different kinds of *bacteriophages* is called *bacteriophage* cocktail. Even among different *bacteriophages* showing equal effect on the same bacteria, there is a difference in the cleavage site of cell wall peptidoglycan and actual functional mechanisms, producing different results. Therefore, co-use of two different *bacteriophages* might be more effective than single, separate use of each *bacteriophage*.

It has been recently attempted to use lytic protein derived from *bacteriophage* to remove biofilm. In general, lytic protein derived from *bacteriophage* exhibits wider spectrum of antibacterial activity than its mother *bacteriophage*. Therefore, it is expected that lytic protein can be more effective in eliminating biofilm than *bacteriophage*. However, it seems too early to judge with such a few reports made so far. And, there is no report disclosing the sufficient biofilm removal activity of lytic protein. In relation to the lytic protein derived from *bacteriophage*, it was once reported that recombinant φ11 endolysin could remove biofilm generated by *Staphylococcus aureus* (Applied and Environmental Microbiology 73: 347-352, 2007). However, the effect of φ11 endolysin was not sufficient because the antibacterial spectrum was still too narrow. To treat biofilm generated by different *Staphylococcus aureus* strains, diverse lytic proteins derived from different *bacteriophages* are required. What we have to keep in our mind herein is that every lytic protein derived from *bacteriophage* is not capable of removing biofilm. According to the previous reports. φ11 endolysin has biofilm removal activity but φ12 endolysin has not. Therefore, biofilm removal activity is not a common property of lytic protein derived from *bacteriophage*. So, it is necessary to obtain diverse lytic proteins derived from *bacteriophage* having biofilm removal activity as well as diverse *bacteriophages*.

DISCLOSURE

Technical Problem

The present inventors provide a composition for eliminating biofilm formed by *Staphylococcus aureus* using *bacteriophage* or lytic protein derived from the *bacteriophage*, and further tried to use the composition for the treatment of disease caused by *Staphylococcus aureus* and then become chronic by biofilm formed thereby.

Particularly, the present inventors tried to develop a composition effective in elimination and treatment of biofilm generated by *Staphylococcus aureus* which is the cause of various biofilm-associated infectious diseases. As a result, the present inventors completed this invention by developing an effective composition for the elimination and treatment of biofilm generated by *Staphylococcus aureus* using the *bacteriophage* first identified by the inventors or lytic protein derived from the *bacteriophage*.

It is an object of the present invention to provide a composition for eliminating biofilm generated by *Staphylococcus aureus* containing *bacteriophage* or lytic protein derived from the *bacteriophage* of the present invention as an active ingredient. The composition of the present invention can additionally include a component confirmed to have antibacterial activity against *Staphylococcus aureus*.

It is another object of the present invention to provide a medical cleaner and an environmental purifier against biofilm-forming *Staphylococcus aureus* which contain *bacteriophage* or lytic protein derived from the *bacteriophage* of the present invention as an active ingredient. The medical cleaner and the environmental purifier herein can additionally include a component confirmed to have antibacterial activity against *Staphylococcus aureus*.

It is further an object of the present invention to provide a therapeutic agent or antibacterial agent capable of improving the treatment effect on biofilm-associated disease caused by biofilm-forming *Staphylococcus aureus* which contains *bacteriophage* or lytic protein derived from the *bacteriophage* of the present invention as an active ingredient. The therapeutic agent or antibacterial agent of the present invention can additionally include a component confirmed to have antibacterial activity against *Staphylococcus aureus*.

Technical Solution

To achieve the above objects, the present inventors completed this invention by confirming that the *bacteriophage* isolated by the inventors and lytic protein prepared using a gene derived from the *bacteriophage* could eliminate biofilm formed by *Staphylococcus aureus*.

The present invention provides a composition for eliminating biofilm generated by *Staphylococcus aureus* containing *bacteriophage* or lytic protein derived from the *bacteriophage* of the present invention as an active ingredient.

The present invention also provides a pharmaceutical composition for the treatment of biofilm-associated disease caused by bifilm forming *Staphylococcus aureus* containing *bacteriophage* or lytic protein derived from the *bacteriophage* of the present invention as an active ingredient. The composition can additionally include a component confirmed to have antibacterial activity against *Staphylococcus aureus*. This additional component does not necessarily have power to destroy extracellular matrix of biofilm.

The present invention further provides a pharmaceutical composition for destroying extracellular matrix of biofilm along with the conventional antibiotics to increase the treatment effect of the conventional antibiotics on biofilm-associated disease caused by biofilm-forming *Staphylococcus aureus* containing *bacteriophage* or lytic protein derived from the *bacteriophage* of the present invention as an active ingredient. The conventional antibiotic included in this composition does not necessarily have power to destroy extracellular matrix of biofilm.

The composition of the present invention is formulated as a disinfectant, a medical cleaner, an environmental purifier, a therapeutic agent and an antibacterial agent for the elimination of biofilm generated by *Staphylococcus aureus* or for the treatment of disease caused by *Staphylococcus aureus* and become chronic by biofilm formed by biofilm-forming *Staphylococcus aureus*. The composition can additionally include a component confirmed to have antibacterial activity against *Staphylococcus aureus*.

Hereinafter, the present invention is described in detail.

The present inventors isolated novel *bacteriophage* capable of killing specifically *Staphylococcus aureus*, and deposited the *bacteriophage* at Korean Agricultural Culture Collection, National Institute of Agricultural Biotechnology on Jun. 14, 2006 (Accession No: KACC 97001P) and at Biological Resource Center, Korea Research Institute of Bioscience and Biotechnology on Jul. 18, 2007 (Accession No: KCTC 11153BP). The related matters have been applied for a patent (Korean Patent Application No. 2006-55461). The present inventors continued the study and as a result isolated another effective *bacteriophage*, and then deposited the isolated *bacteriophage* at Biological Resource Center, Korea Research Institute of Bioscience and Biotechnology on Jul. 18, 2007 (Accession No: KCTC 11154BP), and also applied for a patent for the related matters (Korean Patent Application No. 2007-82358).

In addition, the present inventors applied for a patent describing a novel antibacterial protein originated from the *bacteriophage* capable of killing specifically *Staphylococcus aureus* based on the genetic information thereon (Korean Patent Application No. 2006-73562 and No. 2007-82357).

As described hereinbefore, lytic protein (antibacterial protein) derived from *bacteriophage* is a protein that destroys cell wall of a host bacterium when the *bacteriophage* comes out of the host bacterium. Such lytic protein derived from *bacteriophage* is generally called lysin. The lytic protein, lysin, is composed of N-terminal catalytic domain and C-terminal binding domain and these two domains are linked by a short linker. Lysin can have two different catalytic domains, which is a rare case, though. C-terminal binding domain is conjugated with matrix on cell wall of target bacteria. The difference between the catalytic domain and the binding domain makes the difference in antibacterial spectrum of lytic protein. Therefore, it is also important to secure diverse lytic proteins derived from different *bacteriophages*. Diversity of lytic proteins facilitates establishing a method to cope with more bacteria and combination therapy of at least two different lytic proteins can increase the antibacterial effect, compared with single treatment of one kind of lytic protein.

The present invention provides *bacteriophage* SAP-1 (Accession No. KCTC 11153BP) having a genome represented by the nucleotide sequence selected from the group consisting of sequences represented by SEQ. ID. NO: 1 NO: 26. and *bacteriophage* SAP-2 (Accession No. KCTC 11154BP) having the nucleotide sequence represented by SEQ. ID. NO: 29 which are capable of killing specifically *Staphylococcus aureus* and effective in destroying biofilm formed by *Staphylococcus aureus*.

The present invention also provides lytic protein derived from *bacteriophage* SAP-1 having the amino acid sequence represented by SEQ. ID. NO: 28 and a gene encoding the nucleotide sequence represented by SEQ. ID. NO: 27 and lytic protein derived from *bacteriophage* SAP-2 having the amino acid sequence represented by SEQ. ID. NO: 31 and a gene encoding the nucleotide sequence represented by SEQ. ID. NO: 30 which are capable of killing specifically *Staphylococcus aureus* and effective in destroying biofilm formed by *Staphylococcus aureus*. Herein, the antibacterial activity by lytic activity is not distinguished from the general antibacterial activity resulted from other mechanisms.

The present inventors provide a composition for elimination of biofilm formed by *Staphylococcus aureus* using *bacteriophage* or lytic protein derived from the *bacteriophage* capable of killing specifically *Staphylococcus aureus* and effective in destroying biofilm formed by *Staphylococcus aureus*.

Once biofilm is formed by *Staphylococcus aureus*, as described hereinbefore, it results in chronic infection and the treatment of such chronic infection is very difficult. All the conventional treatment methods based on the conventional antibiotics are not so effective. Particularly, recent rise of antibiotic resistant strains requests a novel method to treat biofilm formed by such antibiotic resistant strains. The present inventors provide an appropriate method to treat such biofilm using *bacteriophage* or lytic protein derived therefrom.

It is another object of the present invention to provide a composition for a medical cleaner and an environmental purifier containing the *bacteriophage* or lytic protein derived from the *bacteriophage* as an active ingredient.

The medical cleaner is used to prevent biofilm from being formed on the surface of artificial organs transplanted or wound. Biofilm formed by *Staphylococcus aureus* is largely found on implanted artificial surfaces such as catheters, heart valves, shunts and prosthetic devices (New Microbiol 22: 337-341, 1999; J Med Microbiol 50: 582-587, 2001; Infections Associated with Indwelling Medical Devices, pp. 55-88, 2000, ASM, Washington, D.C.). Therefore, implantable medical devices are preferably coated with an antibacterial agent.

Once biofilm is formed on artificial implants, surgical operation is the only way to eliminate the biofilm. Therefore, it is more important to prevent biofilm from being formed. The prevention of the formation of biofilm has advantages of less frequent replacement of implanted medical devices and thereby decreases of medical cost.

The medical cleaner can be sprayed on the surface of a target area which needs to be protected from the formation of biofilm, for example artificial joint, catheter, endoscope or wound. Washing can be performed by hand wash, ultrasonic cleaner or automatic washer. Medical devices can be soaked in a medical cleaner. As antibiotic-resistant strains are generated, a novel method to treat biofilms generated by such antibiotic-resistant strains is necessary. Therefore, the present inventors developed an appropriate method using *bacteriophage* or lytic protein derived from the *bacteriophage*.

The use of the composition of the present invention as an environmental purifier indicates the use as a general disinfectant. The composition of the present invention can be effectively used as a disinfectant for cooking area and facilities.

The effective content of *bacteriophage* or lytic protein derived from the *bacteriophage* in the composition of the present invention for a medical cleaner and an environmental purifier can be determined by those in the art after simple preliminary investigation. The dose can be regulated considering a field targeted and a method of application. The content of the *bacteriophage* in the composition of the present invention is preferably $1\times10^3$–$1\times10^{12}$ pfu/ml and more preferably $1\times10^8$–$1\times10^{10}$ pfu/ml. The content of the lytic protein in the composition of the present invention is preferably 0.001% (w/v)-0.1% (w/v), more preferably 0.002% (w/v)-0.01% (w/v) and most preferably 0.005% (w/v). The *bacteriophage* and the lytic protein derived therefrom of the present invention are complementary to each other.

It is further an object of the present invention to provide a therapeutic agent and antibacterial agent containing the *bacteriophage* or lytic protein derived from the *bacteriophage* as an active ingredient.

The *bacteriophage* or lytic protein derived from the *bacteriophage* included in the composition of the present invention, as described hereinbefore, is capable of killing specifically *Staphylococcus aureus* and effective in destroying biofilm formed by *Staphylococcus aureus*, so that it has treatment effect on diverse chronic infectious diseases caused by *Staphylococcus aureus* and become chronic by the formation of biofilm such as mastitis, dermatitis, sepsis, suppurative disorder, food poisoning, pneumonia, osteomyelitis, impetigo, bacteremia, endocarditis, and enteritis, etc. The composition herein can additionally include a component confirmed to have antibacterial activity against *Staphylococcus aureus* to increase treatment effect.

The component confirmed to have antibacterial activity against *Staphylococcus aureus* that can be additionally included in the composition of the present invention is exemplified by methicillin, oxacillin and vancomycin, but not always limited thereto, and diverse antibiotics can be used.

When the *bacteriophage* or lytic protein derived from the same can be co-administered with the conventional antibiotics or other effective substances, it helps them to be as fully functioning as aimed by destroying extracellular matrix of biofilm. The *bacteriophage* or lytic protein derived therefrom of the present invention can digest a specific bond in peptidoglycan structure, unlike lysostaphin, so that it can be effective in treating disease caused by *Staphylococcus aureus* which is not sensitive to lysostaphin or lysostaphin-resistant variants.

The effective dosage of the composition of the present invention as a therapeutic agent or an antibacterial agent can be determined and prescribed by an experienced doctor. In this invention, 'antibacterial agent' is the generalized term for antiseptics, bactericides and antibiotics. The effective dose can be specifically determined by considering age and weight of an animal including human, clinical symptoms and administration methods.

The effective dosage of the pharmaceutical composition of the present invention formulated for application, spray, injection and general administration can be determined by considering formulation method, administration method, age, weight and gender of a patient, severity of a disease, diet, administration time and pathway, excretion rate and reactivity, etc. An experienced doctor can determine and prescribe the effective dosage considering the purpose of treatment. In general, the content of the *bacteriophage* in the pharmaceutical composition of the present invention is preferably $1\times10^3$-$1\times10^{12}$ pfu/ml, and more preferably $1\times10^8$-$1\times10^{10}$ pfu/ml. And the content of the lytic protein in the pharmaceutical composition of the present invention is preferably 0.001% (w/v)-0.1% (w/v), more preferably 0.002% (w/v)-0.01% (w/v) and most preferably 0.005% (w/v). The *bacteriophage* and lytic protein derived from the same of the present invention are complementary to each other.

The composition of the present invention can be applied, sprayed or injected on a target area. In addition, the composition of the present invention can be orally or parenterally administered. The parenteral administration is exemplified by intravenous administration, intraperitoneal administration, intramuscular administration, hypodermic administration or local administration.

The pharmaceutically acceptable carrier included in the composition of the present invention is exemplified by lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate and mineral oil, but not always limited thereto. The pharmaceutical composition of the present invention can additionally include lubricants, wetting agents, sweetening agents, flavors, emulsifying agents, suspending agents and adjuvants, in addition to the above ingredients.

The pharmaceutical composition of the present invention can be formulated by using a pharmaceutically acceptable carrier and/or excipient according to a method generally performed by those in the art as a unit dose or in a multi-close container. At this time, the formulation can be oil or solution in aqueous media, suspension or emulsion, extract, powder, granule, tablet or capsule and a dispersing agent or a stabilizer can be additionally included therein.

The treatment of disease caused by *Staphylococcus aureus* using the *bacteriophage* capable of destroying biofilm or lytic protein derived from the *bacteriophage* is advantageous over the conventional antibiotics based treatment. That is, biofilm removal and target bacteria destruction can be achieved at the same time by the treatment method using the *bacteriophage* or lytic protein derived from the same. So, even if *Staphylococcus aureus* survives in biofilm, it can be effectively destroyed.

The term 'treatment' in this invention indicates (i) prevention of infectious disease caused by *Staphylococcus aureus*; (ii) inhibition of infectious disease caused by *Staphylococcus aureus* and (iii) alleviation of infectious disease caused by *Staphylococcus aureus*.

Advantageous Effects

As explained hereinbefore, *bacteriophage* SAP-1, *bacteriophage* SAP-2 and lytic proteins derived from those *bacteriophages* of the present invention are capable of killing *Staphylococcus aureus* specifically and further destroying biofilm formed by *Staphylococcus aureus*, so that they can be effectively used for the elimination of biofilm by *Staphylococcus aureus*. They can be also used as a medical cleaner and an environmental purifier for removing biofilm formed by *Staphylococcus aureus* and further as a therapeutic agent and an antibacterial agent with improved treatment effect by removing biofilm of *Staphylococcus aureus* for the treatment of infection caused by biofilm-forming *Staphylococcus aureus*.

And, *bacteriophage* SAP-1, *bacteriophage* SAP-2 and lytic proteins derived from those *bacteriophages* of the present invention not only have *Staphylococcus aureus* specific killing activity but also have biofilm removal activity. Therefore, when they are administered with the conventional antibiotics or medicines, they can increase treatment effect of the conventional antibiotics or medicines having antibacterial activity against *Staphylococcus aureus* which have been not so effective in treatment because of being blocked by extracellular matrix of biofilm formed by *Staphylococcus aureus*.

DESCRIPTION OF DRAWINGS

The application of the preferred embodiments of the present invention is best understood with reference to the accompanying drawings, wherein.

Best Mode

Figure 1:
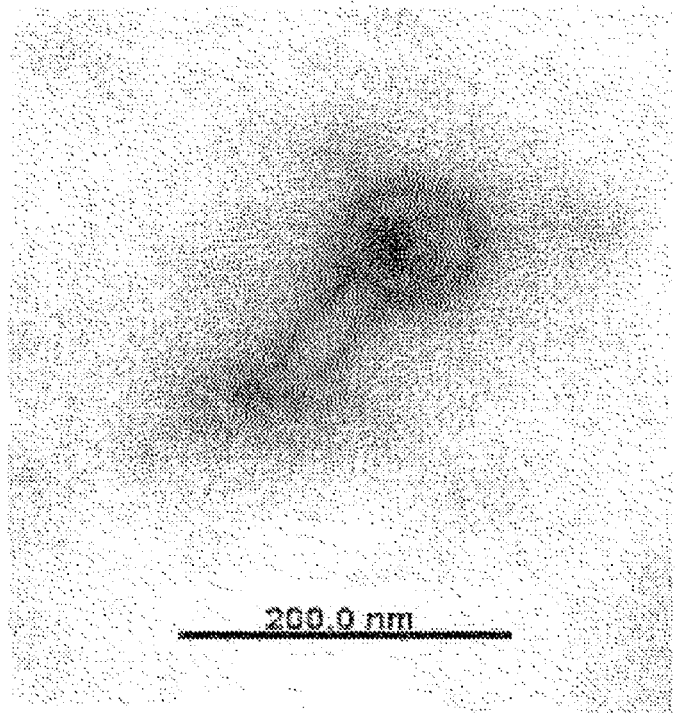
FIG. 1 is a set of electron microscope photographs showing the *Staphylococcus aureus* specific *bacteriophage* isolated by plaque assay. (A): Myoviridae family T4-like phage genus *bacteriophage*, (B): Podoviridae family φ29-like virus genus *bacteriophage*.
Figure 1:
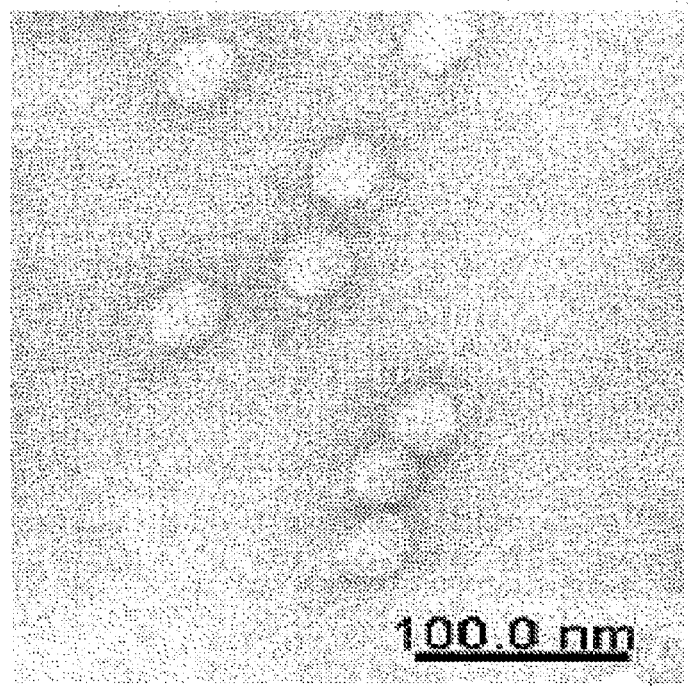

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Isolation of *Staphylococcus aureus* from Pathogen and Isolation of *Bacteriophage* Having *Staphylococcus aureus* Specific Killing Ability <1-1> Isolation of *Staphylococcus aureus*

Bacteriophage is distributed widely in nature and particularly lives together with bacteria. To isolate *bacteriophage* infecting *Staphylococcus aureus* specifically, the present inventors collected samples from expected places where *Staphylococcus aureus* seems to proliferate, followed by confirmation if *Staphylococcus aureus* was growing therein by using Baird-Packer agar medium, the *Staphylococcus aureus* selection medium.

Particularly, bovine mastitis was selected as a target disease to isolate the target bacteria *Staphylococcus aureus* from pathogen. Mastitis is one of the most representative diseases caused by *Staphylococcus aureus*. *Staphylococcus aureus* was isolated from the samples extracted from milk of milk-cow with mastitis by using Baird-Parker agar medium, the *Staphylococcus aureus* selection medium. Then, the isolated bacteria were identified as *Staphylococcus aureus* by Gram staining method. catalase test and biochemical test using Vitek (bioMerieux). The results are shown in Table 1.

TABLE 1

| Vitek ID | 200000-0 (A1-18) catalase + Coagulase + |
| Type | Gram positive identification card (GPI) |
| Condition | Final |
| Time | 5 hours |
| Organism | *Staphylococcus aureus* |

| PB+ | BAC− | OPT+ | HCS+ | 6NC+ | 10B+ |
|---|---|---|---|---|---|
| 40B− | ESC− | ARG− | URE− | TZR+ | NOV− |
| DEX+ | LAC+ | MAN+ | RAF− | SAL− | SOR− |
| SUC+ | TRE+ | ARA− | PYR+ | PUL− | INU− |
| MEL− | MLZ− | CEL− | RIB− | XYL− | CAT+ |
| BH/CO+ | | | | | |

<1-2> Isolation of *Staphylococcus aureus* Specific *Bacteriophage*

Next, to isolate a *Staphylococcus aureus* specific *bacteriophage*, the samples expected to contain *bacteriophage* were cultured with *Staphylococcus aureus*. The culture broth was centrifuged to obtain supernatant. The obtained supernatant was filtered. The filtered solution was cultured again with the cultured *Staphylococcus aureus* as bait for isolating *bacteriophage*, followed by investigation of lysis of *Staphylococcus aureus*. The lysis of *Staphylococcus aureus* was finally confirmed by plaque assay.

Particularly, to isolate *bacteriophage* having *Staphylococcus aureus* specific killing activity, samples were collected from soil, straws, earth and sewage in cowshed where *bacteriophage* possibly survives. The samples were shaking-cultured at 37° C. for 3-4 hours with the *Staphylococcus aureus* obtained in Example <1-1>. After cultivaton, the culture broth was centrifuged at 8,000 rpm for 20 minutes to obtain supernatant. The supernatant was filtered with 0.45 μm filter. Two kinds of *Staphylococcus aureus* specific *bacteriophages* were isolated by plaque assay with the filtrate.

To observe morphology of the obtained *bacteriophage*, the *bacteriophage* was purified by CsCl density gradient (density: 1.15 g/ml, 1.45 g/ml, 1.50 g/ml and 1.70 g/ml) centrifugation (38,000 rpm, 22 hours, 4° C.). The purified bacteriophage was placed on cupper grid, followed by negative staining with 2% uranyl acetate and drying. Morphology of the *bacteriophage* was photographed under electron microscope. As a result, the isolated *bacteriophages* were confirmed according to morphological classification to belong to Myoviridae family T4-like phage genus and Podoviridae family φ29-like virus genus (FIG. 1). The isolated *bacteriophage* belonging to Myoviridae family T4-like phage genus was named *bacteriophage* SAP-1, which was deposited at Korean Agricultural Culture Collection, National Institute of Agricultural Biotechnology on Jun. 14, 2006 (Accession No: KACC 97001P) and at Biological Resource Center, Korea Research Institute of Bioscience and Biotechnology on Jul. 18, 2007 (Accession No: KCTC 11153BP). Another *bacteriophage* isolated above belonging to Podoviridae family φ29-like virus genus was named *bacteriophage* SAP-2, which was deposited at Biological Resource Center, Korea Research Institute of Bioscience and Biotechnology on Jul. 18, 2007 (Accession No: KCTC 11154BP).

EXAMPLE 2

Genetic Characteristics of the *Staphylococcus Aureus* Specific *Bacteriophages* SAP-1 and SAP-2

<2-1> Genetic Characteristics of *Bacteriophage* SAP-1

Genetic characteristics of the isolated *bacteriophage* SAP-1 were analyzed. First, *bacteriophage* genome was extracted by the conventional method, followed by genetic analysis. Particularly, 50 ml of *Staphylococcus aureus* suspension [$OD_{600}$: 1] and 1 ml of *bacteriophage* suspension filtered at the concentration of $1 \times 10^8$ pfu/ml were inoculated to 200 ml of TSB (Tryptic Soy Broth) medium (casein digest, 17 g/l soybean digest, 3 g/l dextrose, 2.5 g/l NaCl, 5 g/l dipotassium phosphate, 2.5 g/) in 1 l flask, followed by shaking-culture at 37° C. for 3-4 hours. Upon completion of the culture, lysis of the *Staphylococcus aureus* was investigated. When lysis of the *Staphylococcus aureus* was confirmed, the culture broth was filtered with 0.45 μm filter. Then, 20% polyethylene glycol 8000/2.5 M NaCl solution was added to the filtrate by ⅙ of the filtrate volume, which stood at 4° C. for overnight. The solution was centrifuged at 8,000 rpm for 20 minutes to obtain *bacteriophage* from the precipitate. The obtained *bacteriophage* precipitate was suspended in 1 ml PBS (phosphate buffer saline), to which 20% polyethylene glycol 8000/2.5 M NaCl solution was added by ⅙ the total volume, which stood at 4° C. for one hour. One hour later, the solution was centrifuged at 14,000 for 10 minutes to obtain purified *bacteriophage* precipitate. The precipitate was mixed with 200 ml of iodide buffer (10 mM Tris-HCl (pH 8.0), 1 mM EDTA, 4 M NaI) gently, which stood at room temperature for 15 minutes. *Bacteriophage* genome was extracted by using DNeasy Tissue kit (QIAGEN) and PCR purification kit (Labopass).

Figure 2:
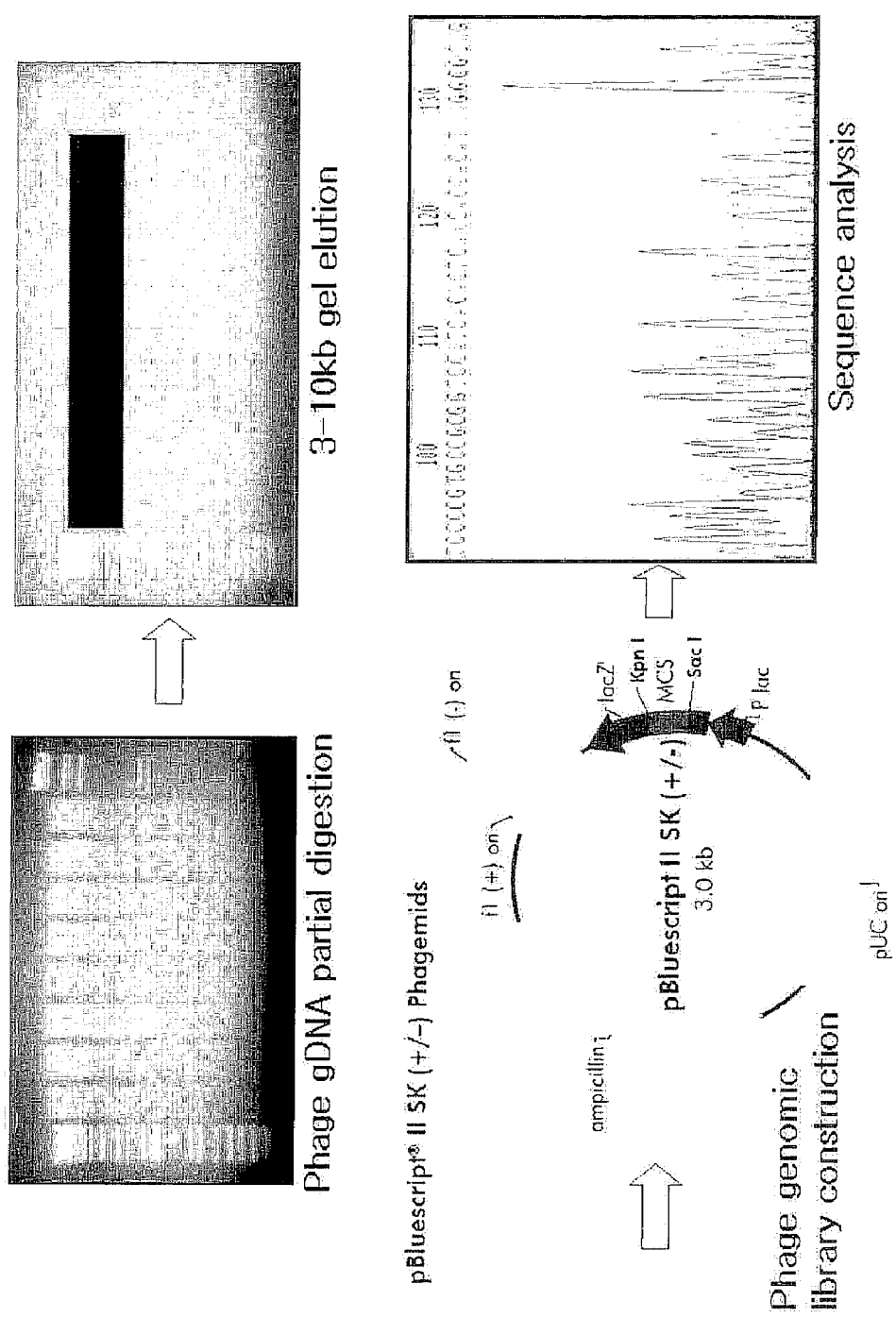
FIG. 2 is a schematic diagram illustrating the method for construction of *bacteriophage* genome library stepwise.

The extracted *bacteriophage* genome was genomic DNA (gDNA). The total gDNA size was too big to analyze its sequence directly. So, gDNA library was first constructed, followed by sequencing. The gDNA library was constructed by using the restriction enzyme Msp I according to the conventional method presented in FIG. 2.

Particularly, to obtain various gene fragments, the extracted gDNA was treated with the restriction enzyme Msp I at 30° C. for one minute, leading to partial fragmentation of the gDNA. After the fragmentation, the gene fragments were introduced into pBluescript II SK(+) phagemid vector (Stratagene) using T4 ligase. The constructed recombinant plasmid containing *bacteriophage* gene fragments was introduced into *E. coli* Top10F' (Invitrogen) by electroporation, one of electro-transformation methods. The transformant having the recombinant plasmid was selected on ampicillin containing agar plate supplemented with X-Gal (5-bromo-4-chloro-3-indolyl-beta-D-galactopyranoside) and IPTG (isopropyl-D-1-thiogalactopyranoside) by Blue-White colony selection. The selected single colony was inoculated in the culture medium containing ampicillin, followed by shaking-culture for overnight. Plasmid was extracted from the cultured cells by using plasmid purification kit (iNtRON Biotechnology). The extracted plasmid was electrophoresed on 0.8% agarose gel to examine the size. Based on the confirmed size, the recombinant plasmid was selected.

The selected plasmids were 51 in all and whose corresponding clones were also 51. These clones were cultured again, from which plasmids were extracted again. Nucleotide sequences of the extracted plasmids were analyzed. Sequencing was performed with M13 forward primer and M13 reverse primer which are general primers widely used for sequencing. Each primer sequence is shown in Table 2.

TABLE 2

| Primer | Sequence |
|---|---|
| M13 forward primer | GTCGTGACTGGGAAAACCCTGGCG (SEQ ID NO: 32) |
| M13 reverse primer | TCCTGTGTGAAATTGTTATCCGCT (SEQ ID NO: 33) |

The gene sequences obtained thereby are partial sequences forming the whole genome of bacteriophage SAP-1, which are represented by SEQ. ID. NO: 1 NO: 26.

Homology of the nucleotide sequences of bacteriophage SAP-1 with the known bacteriophage genes was analyzed by using BLAST on Web (http://www.ncbi.nlm.nih.gov/BLAST/). As a result, the nucleotide sequence of the bacteriophage SAP-1 was confirmed to have the highest homology with the bacteriophage G1. To understand genetic functions of each part of the genome, ORF (Open Reading Frame) analysis was performed based on bacteriophage G1 gene sequence using NCBI ORF finder (http://www.ncbi.nlm.nih.gov/gorf/gorf.html) and Vector NTI ContigExpress (INFORMAX) program. As a result, gene sequence of the lytic protein of bacteriophage SAP-1 was obtained. The whole nucleotide sequence of the lytic protein derived from bacteriophage SAP-1 is represented by SEQ. ID. NO: 27. And the amino acid sequence of the lytic protein derived from bacteriophage SAP-1 is represented by SEQ. ID. NO: 28. The lytic protein derived from bacteriophage SAP-1 was named as SAL-1.

<2-2> Genetic Characteristics of Bacteriophage SAP-2

Genetic characteristics of the isolated bacteriophage SAP-2 were analyzed. First, the genome of bacteriophage SAP-2 was extracted by the conventional method, followed by genetic analysis. Particularly, 50 ml of Staphylococcus aureus suspension ($OD_{600}$: 1) and 1 ml of bacteriophage suspension filtered at the concentration of $1\times10^8$ pfu/ml were added to 200 ml of TSB medium in 1 l flask, followed by shaking-culture at 37° C. for 3-4 hours. Upon completion of the culture, lysis of the Staphylococcus aureus was investigated. When lysis of the Staphylococcus aureus was confirmed, the culture broth was filtered with 0.45 µm filter. To eliminate DNA and RNA of Staphylococcus aureus remaining in the filtered culture broth, 200 U of each DNase I and RNase A were added to 10 ml of the filtered culture broth, which stood at 37° C. for 30 minutes. To inactivate DNase I and RNase A, 500 µl of 0.5 M EDTA (ethylenediaminetetraacetic acid) was added, which stood for 10 minutes. Next, to destroy the outer protein envelope of bacteriophage, 100 µl of proteinase K (20 mg/ml) and 500 µl of 10% SDS (Sodium Dodecyl Sulfate) were added thereto, followed by incubation at 65° C. for 1 hour. After one hour incubation, 10 ml of the mixed solution comprising phenol, chloroform and isoamylalcohol (25:24:1) was added thereto and mixed well. The mixture was centrifuged at 18,000 rpm to separate layers. The upper layer was recovered, to which 100% alcohol was added double the volume of the recovered upper layer, followed by extraction of pure genome.

The extracted bacteriophage genome was gDNA. The gDNA of bacteriophage SAP-2 was sequenced directly since the gDNA was not too big.

Primers used for the direct sequencing of bacteriophage SAP-2 gDNA are shown in Table 3.

TABLE 3

| Primer | Sequence | |
|---|---|---|
| T7 promoter | TAATACGACTCACTATAGGGCGA | (SEQ ID NO: 34) |
| SP6 promoter | GTATTCTATAGTGTCACCTAAAT | (SEQ ID NO: 35) |
| 1 | CGTAATGCTTCAAAATGTTC | (SEQ ID NO: 36) |
| 2 | GAGCAATGTTAGTTGATTACTCATT | (SEQ ID NO: 37) |
| 3 | CCATTTAAAAAATAATCATCACGTT | (SEQ ID NO: 38) |
| 4 | TGCAATTCATATATTAGATGATAA | (SEQ ID NO: 39) |
| 5 | TATGCTTTATATGGAGGTTGATAAC | (SEQ ID NO: 40) |
| 6 | AATTAGTGTACCGTCACCTAAAGA | (SEQ ID NO: 41) |
| 7 | TGCAACACCATCGTGATGTA | (SEQ ID NO: 42) |
| 8 | GTTGTTGAACATCGCAACAG | (SEQ ID NO: 43) |
| 9 | CAAAATCTGATAAAAACGTCAT | (SEQ ID NO: 44) |
| 10 | GACGTGATGAGGATTATTAT | (SEQ ID NO: 45) |
| 11 | ATAAATTCTCTTTCTTTTTCCTCAAATTCAAATCTCGCTAATGT | (SEQ ID NO: 46) |
| 12 | CATACGTGGATAATTACGTTTCAACATTAATTCCTCATTT | (SEQ ID NO: 47) |
| 13 | ATCAAATTCATTTAAAATTTTCTTTCT | (SEQ ID NO: 48) |
| 14 | AATGTCACCTATGTTTAATGCAGA | (SEQ ID NO: 49) |
| 15 | AGTTCATCATTTAAGAATTGAACAACAGAACT | (SEQ ID NO: 50) |
| 16 | TTTGTTGCTCTAATGATGTAATACGTTGTTCTAATATAACAG | (SEQ ID NO: 51) |
| 17 | TCACTTGCAATAATACCACTTTCTAAT | (SEQ ID NO: 52) |
| 18 | GTCAAGTATCATTTTAATACAATTT | (SEQ ID NO: 53) |
| 19 | TCATTATACATTACGTGACGCTTA | (SEQ ID NO: 54) |
| 20 | AGCTTCTCTTTCTTTTTTCCATCTA | (SEQ ID NO: 55) |
| 21 | GAACTTCATTGTATTTAGCGCTGTTG | (SEQ ID NO: 56) |
| 22 | TGAATCTTCATATGGTCGACCTGCAG | (SEQ ID NO: 57) |
| 23 | ATTTAATAGTTTTGCACAAGTACCAA | (SEQ ID NO: 58) |
| 24 | CAAACTAACCCATCTGATAAACAAAC | (SEQ ID NO: 59) |
| 25 | AACCTAATGGCTATTGGTTCCAACCA | (SEQ ID NO: 60) |
| 26 | GGTAACAGTTCAGTTAATTCACAT | (SEQ ID NO: 61) |
| 27 | GGTGCCATAATTTATTATTCCTCC | (SEQ ID NO: 62) |
| 28 | TTAATCGTACCTAATTTAATATCAC | (SEQ ID NO: 63) |
| 29 | AACGTAAATCGTTATTACTTGCAATG | (SEQ ID NO: 64) |
| 30 | CGTTACAACACCCGGAGAATATTA | (SEQ ID NO: 65) |
| 31 | CCAAATGTCCAAGATTTTGAATAA | (SEQ ID NO: 66) |
| 32 | TTTAAAATGTACAGGTACGTATAC | (SEQ ID NO: 67) |

TABLE 3-continued

| Primer | Sequence | |
|---|---|---|
| 33 | TTGAATTTAACGAATATAATTTGGC | (SEQ ID NO: 68) |
| 34 | ATATTATCATGATTGCACATAACTG | (SEQ ID NO: 69) |
| 35 | GTAAAAGGTTATGGACGTTTTAAT | (SEQ ID NO: 70) |
| 36 | AATTTTTATGACTATATAAAATCATT | (SEQ ID NO: 71) |
| 37 | ACAAAAAACATTTAACAACACGTAT | (SEQ ID NO: 72) |
| 38 | AAATAAAATACAAAACATAATCAAT | (SEQ ID NO: 73) |

Nucleotide sequence of the whole genome of bacteriophage SAP-2 is represented by SEQ. ID. NO: 29. Total number of nucleotides forming the genome of bacteriophage SAP-2 is 17938.

Homology of the nucleotide sequence of bacteriophage SAP-2 with the known bacteriophage genes was analyzed by using BLAST on Web. As a result, homology of the analyzed nucleotide sequence of the bacteriophage SAP-2 was 86.0% with Staphylococcus aureus phage phi P68, 81.1% with 44AHJD and 49.2% homology with bacteriophage 66. To understand genetic functions of each part of the genome, ORF analysis was performed based on Staphylococcus aureus phage phi P68 gene sequence exhibiting the highest homology by using NCBI ORF finder and Vector NTI ContigExpress program. Comparing with the paper 'Complete nucleotide sequence and molecular characterization of two lytic Staphylococcus aureus phages: 44AHJD and P68, FEMS Microbiology Letters, 2003, 219: 275-283', ORF homology was investigated. As a result, gene sequence of the lytic protein of bacteriophage SAP-2 was obtained. The gene encoding the lytic protein of bacteriophage SAP-2 was composed of 750 bp and the lytic protein expressed therefrom was composed of 250 amino acids. The sequence of the gene encoding the lytic protein of bacteriophage SAP-2 is represented by SEQ. ID. NO: 30 and the amino acid sequence of the lytic protein of bacteriophage SAP-2 is represented by SEQ. ID. NO: 31. The lytic protein derived from bacteriophage SAP-2 was named as SAL-2.

EXAMPLE 3

Cloning of Lytic Protein Gene and Construction of Expression Plasmid

<3-1> Construction of the Lytic Protein SAL-1 Expression Plasmid

From the gene sequencing and ORF analysis performed in Example <2-1>, gene sequence of the lytic protein SAL-1 was identified. To express the target lytic protein from the lytic protein gene, a large-scale expression system of lytic protein was constructed using pBAD-TOPO vector (Invitrogen). The gene of lytic protein was subcloned into the Nco I and Not I restriction enzyme sites of vector according to the conventional method. Before the cloning, enterokinase cleavage site in pBAD-TOPO vector was eliminated and instead Not I restriction enzyme site was inserted. The constructed lytic protein expression plasmid was named pBAD-TOPO-SAL1. E. coli BL21 (DE3) (Novagen) was transformed with the lytic protein expression plasmid, resulting in the preparation of a producing strain of the lytic protein. The producing strain of the lytic protein prepared thereby was deposited at Biological Resource Center, Korea Research Institute of Bioscience and Biotechnology on Jul. 18, 2007 (Accession No: KCTC 11151BP).

<3-2> Construction of the Lytic Protein SAL-2 Expression Plasmid

From the gene sequencing and ORF analysis performed in Example <2-2>, gene sequence of the lytic protein SAL-2 was identified. To express the target lytic protein from the lytic protein gene, a large-scale expression system of lytic protein was constructed using pBAD-TOPO vector (Invitrogen). The gene of lytic protein was subcloned into the Nco I and Not I restriction enzyme sites of vector according to the conventional method. Before the cloning, enterokinase cleavage site in pBAD-TOPO vector was eliminated and instead Not I restriction enzyme site was inserted. The constructed lytic protein expression plasmid was named pBAD::lysinM. E. coli. Origami (DE3) (Novagen) was transformed with the lytic protein expression plasmid, resulting in the preparation of a producing strain of the lytic protein. The producing strain of the lytic protein prepared thereby was deposited at Biological Resource Center, Korea Research Institute of Bioscience and Biotechnology on Jul. 18, 2007 (Accession No: KCTC 11152BP).

EXAMPLE 4

Over-Expression of Lytic Protein

Lytic protein was over-expressed in E. coli transformed with the recombinant plasmid constructed in Example 3. Methods for over-expression of both SAL-1 and SAL-2 are similar. The pBAD-TOPO vector based expression system is the method inducing over-expression using L-arabinose, which is a suitable expression system of toxic protein to host bacteria (according to the manufacturer's instruction titled 'pBAD expression system' and protocol #25-0257 publicized in 2004).

Figure 3:
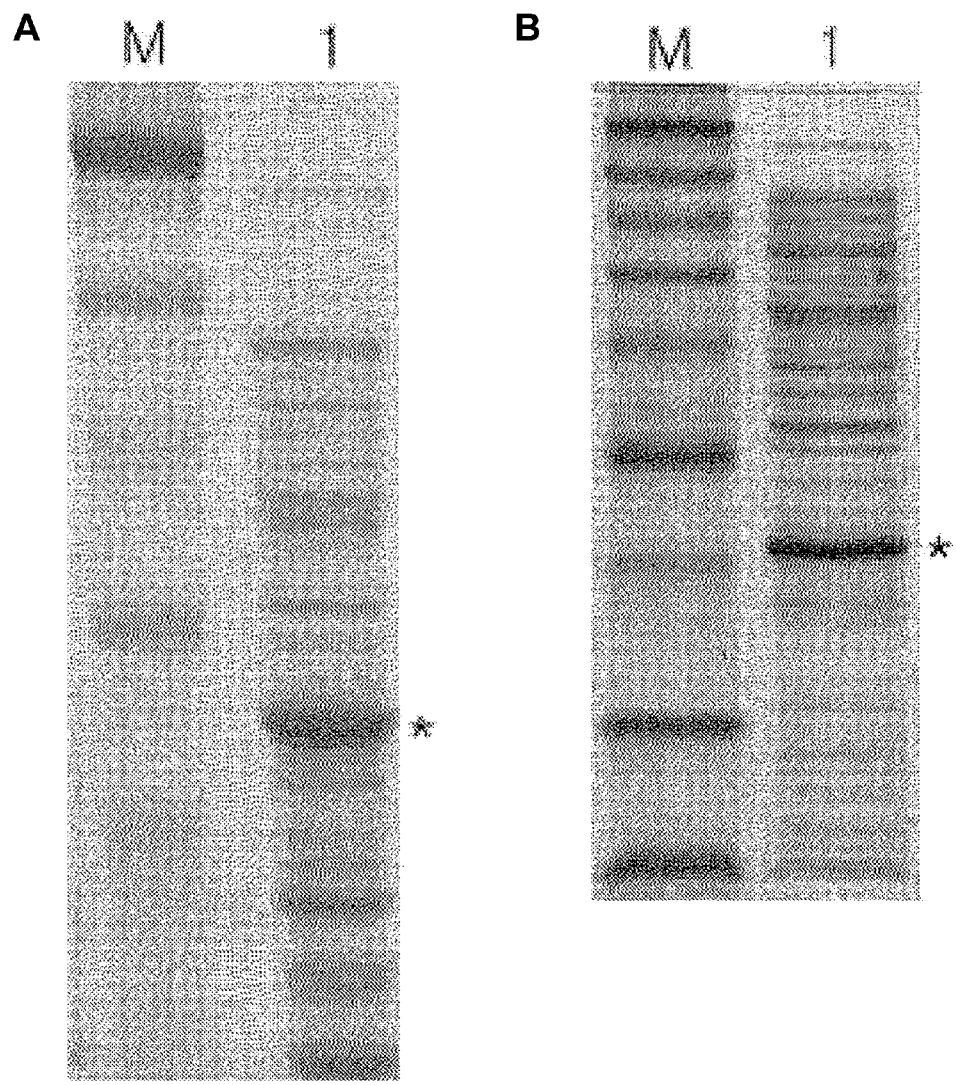
FIG. 3 is a set of photographs illustrating the result of electrophoresis with the expressed lytic protein. (A) lane M: size marker (198, 115, 90.5, 61.5, 46.2, and 37.8 kDa), lane 1: cell lysate containing expressed lytic protein SAL-1 (B) lane M: size marker (198, 115, 90.5, 61.5, 46.2, 37.8, 26, 18.5, and 9 kDa), lane 1: cell lysate containing expressed lytic protein SAL-2. *: over-expressed lytic protein.

Over-expression of lytic proteins is described in detail hereinafter. The constructed plasmids contained ampicillin resistant gene, so every culture medium was supplemented with ampicillin. To express the lytic protein SAL-2. Origami (DE3) was used as a producing strain. This producing strain itself contained tetracycline resistant gene. So, to express the lytic protein SAL-2, every culture medium was supplemented with both of ampicillin and tetracycline. LB medium (trypton, 10 g/L; yeast extract, 5 g/L; NaCl, 10 g/L) was used as a culture medium. Each producing strain of the lytic protein was inoculated in 5 ml of LB medium supplemented with proper antibiotics, followed by shaking-culture at 37° C. for overnight. 100 µl of each overnight culture broth was re-inoculated in 10 ml of fresh LB medium supplemented with proper antibiotics, followed by shaking-culture again at 37° C. Induction was carried out with 0.2% L-arabinose, at which point the cell density ($OD_{600}$) was 0.8-1 (for lytic protein SAL-1) or 0.5 (for lytic protein SAL-2). To induce the expression of the lytic protein SAL-1, temperature for culture was maintained at 37° C. and to induce the lytic protein SAL-2, temperature for culture was changed to 23° C. right after the induction started. The additional culture time for inducing the expression of SAL-1 was 4 hours and 12 hours for the expression of SAL-2. Upon completion of the culture, 1 ml of the cell culture broth was centrifuged at 8,000 rpm for 5 minutes, and then cell precipitate was recovered. The cells were lysed by adding 100 µl of 1% SDS solution to the cell precipitate. 12 µl of the cell lysate was used as a sample for electrophoresis. Precisely, 3 µl of 5x sample loading buffer used for electrophoresis was added to the cell lysate, which was well mixed and boiled in water bath for 5 minutes. Electrophoresis was performed according to the conventional method. Then, the over-expressed lytic protein was confirmed. The results are shown in FIG. 3.

EXAMPLE 5

Separation and Purification of Expressed Lytic Protein

<5-1> Separation and Purification of SAL-1

500 ml of the culture broth of the transformant cultivated in LB medium was centrifuged at 8,000 rpm for 5 minutes to obtain cell precipitate. The precipitate was suspended in 6 ml of 20 mM sodium phosphate buffer (pH 6.0) containing 1 mM phenylmethylsulfonyl fluoride. To precipitate the ribosomal proteins, 2 mg of streptomycin sulfate was added thereto. Cells of the prepared cell suspension were disrupted by sonication. Sonication was performed by repeating 20 second sonication-5 second rest for 20 minutes. The resultant whole cell lysate was centrifuged at 8,000 for 5 minutes to remove the cell debris. The supernatant obtained by the centrifugation proceeded to 35% (w.v) ammonium sulfate precipitation, leading to the concentration of expressed lytic protein. Precisely, ammonium sulfate was added at the final concentration of 35% (w/v), and the mixed solution stood in ice for 15 minutes to precipitate the protein. Then, the mixed solution was centrifuged at 10,000×g for 15 minutes to obtain precipitate. The precipitate was dissolved in 2 ml of adsorption buffer (50 mM sodium phosphate, 0.25 M sodium chloride, pH 6.5) to be used for chromatography. To remove the excessive ammonium sulfate, the prepared protein solution was dialyzed against adsorption buffer at 4° C. for overnight by replacing the adsorption buffer with a fresh buffer from time to time. Upon completion of dialysis, the protein solution was centrifuged at 10,000×g for 25 minutes to eliminate insoluble materials. The protein solution was filtered with 0.2 μm filter, followed by cation-exchange chromatography. CM-Sephadex C-50 (Pharmacia) was used as a cation-exchange resin, which was a weak cation-exchange resin. The column was packed with CM-Sephadex C-50 by 27 cm and the total packed bedvolume was approximately 14 ml. After equilibrium of the column with adsorption buffer, chromatography was performed. The protein solution was loaded on the column, which was washed with 100 ml of adsorption buffer. Other proteins derived from *E. coli* except the lytic protein were hardly adhered on the resin filled in the column. At last, the lytic protein was eluted by using 50 mM sodium phosphate solution (pH 6.5) containing NaCl with increasing the concentration from 0.2 M to 0.8 M. To remove NaCl used for the elution of the lytic protein, the eluent fraction containing the lytic protein was dialyzed against 50 mM of sodium phosphate solution (pH 6.5) at 4° C. for overnight by replacing the sodium phosphate solution with fresh sodium phosphate solution from time to time. The dialysate was concentrated by dialyzing to dried ethylene glycol 20,000.

<5-2> Separation and Purification of SAL-2

500 ml of the culture broth of the transformant cultivated in LB medium was centrifuged at 8,000 rpm for 5 minutes to obtain cell precipitate. The precipitate was suspended in 6 ml of 80 mM Tris-HCl buffer (pH 4.0). Cells of the prepared cell suspension were lysed by freezing/thawing. Precisely, for the freezing/thawing, the cell suspension was frozen by using liquid nitrogen, which was thawed at 30° C. for 5 minutes. This freezing/thawing was repeated 8 times. And the resultant cell lysate was centrifuged at 8,000 rpm for 5 minutes to remove the cell debris. The supernatant obtained by the centrifugation proceeded to 30% (w.v) ammonium sulfate precipitation, leading to the concentration of expressed lytic protein. Precisely, ammonium sulfate was added at the final concentration of 30% (w/v), and the mixed solution stood in ice for 15 minutes to precipitate the protein. Then, the mixed solution was centrifuged at 10,000×g for 15 minutes to obtain precipitate. The precipitate was dissolved in 2 ml of adsorption buffer (25 mM sodium phosphate, pH 5.8) to be used for chromatography. To remove the excessive ammonium sulfate, the prepared protein solution was dialyzed against adsorption buffer at 4° C. for overnight by replacing the adsorption buffer with a fresh buffer from time to time. Upon completion of dialysis, the protein solution was centrifuged at 10,000×g for 25 minutes to eliminate insoluble materials. The protein solution was filtered with 0.2 μm filter, followed by cation-exchange chromatography. HiTrap SPFF (GE Healthcare) was used as a cation-exchange resin, which was a strong cation-exchange resin. After equilibrium of the column with adsorption buffer, chromatography was performed. The protein solution was loaded on the column, which was washed with 100 ml of adsorption buffer. Other proteins derived from *E. coli* except the lytic protein were hardly adhered on the resin filled in the column. At last, the lytic protein was eluted by using 25 mM sodium phosphate solution (pH 5.8) containing KCl with increasing the concentration from 0.2 M to 0.8 M. To remove KCl used for the elution of the lytic protein, the eluent fraction containing the lytic protein was dialyzed against 25 mM of sodium phosphate solution (pH 5.8) at 4° C. for overnight by replacing the sodium phosphate solution with fresh sodium phosphate solution from time to time. The dialysate was concentrated by dialyzing to dried ethylene glycol 20,000.

EXAMPLE 6

Antibacterial Activity of the Lytic Proteins

Antibacterial activity of the lytic proteins separated/purified in Example 5 was investigated. *Staphylococcus aureus* isolated and identified by the present inventors by the same manner as described in Example 1 was used for this experiment.

Figure 4:
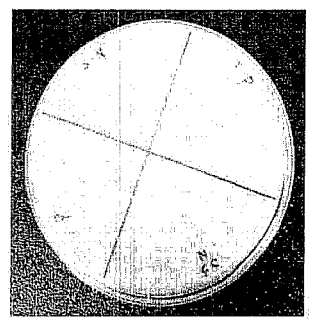
FIG. 4 is a set of photographs illustrating the lytic activity of the lytic protein against *Staphylococcus aureus* isolated clinically, in which clear zones are generated by lytic activity of the lytic protein.
Figure 4:
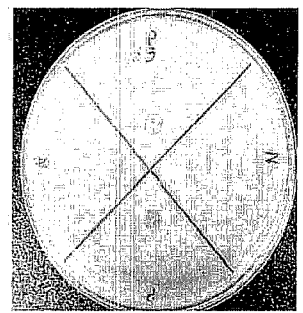

1 ml culture broth of *Staphylococcus aureus* cultivated in TSB medium ($OD_{600}$: 1) was spread on each plate medium, followed by drying. 5 μl of protein solution containing the lytic protein prepared above was dropped thereto, followed by incubation in a 37° C. incubator for overnight. Then, lysis of *Staphylococcus aureus* isolated was examined. As a result, as shown in FIG. 4, it was confirmed that clear zones were formed by the lytic activity of the lytic proteins.

EXAMPLE 7

Biofilm Removal Activity

<7-1>: Selection of Biofilm-Forming *Staphylococcus aureus*

To investigate whether the composition containing *bacteriophage* or lytic protein derived from the *bacteriophage* was capable of destroying biofilm, *Staphylococcus aureus* capable of forming biofilm was selected at first. To select *Staphylococcus aureus* capable of forming biofilm, the existence of genes involved in the formation of biofilm were analyzed first. Precisely, PIA (polysaccharide intercellular adhesion) is important for the formation of biofilm (Science 284: 1523-1527, 1999). And ica C (1054 bp) gene is involved in PIA biosynthesis (J Clin Microbiol 39: 2151-2156, 2001; Infect Immun 67: 5427-5433, 1999). So, to select biofilm-forming *Staphylococcus aureus*, PCR amplification of the ica C gene was performed with the genomic DNA prepared from three kinds of *Staphylococcus aureus* strains. Primers for PCR were prepared as follows.

TABLE 4

| Primer | Sequence | |
|---|---|---|
| Ica C F | ATGAAAAAGATTAGACTTGAACTC | (SEQ ID NO: 74) |
| Ica C R | TTAATAAGCATTAATGTTCAATT | (SEQ ID NO: 75) |

Figure 5:
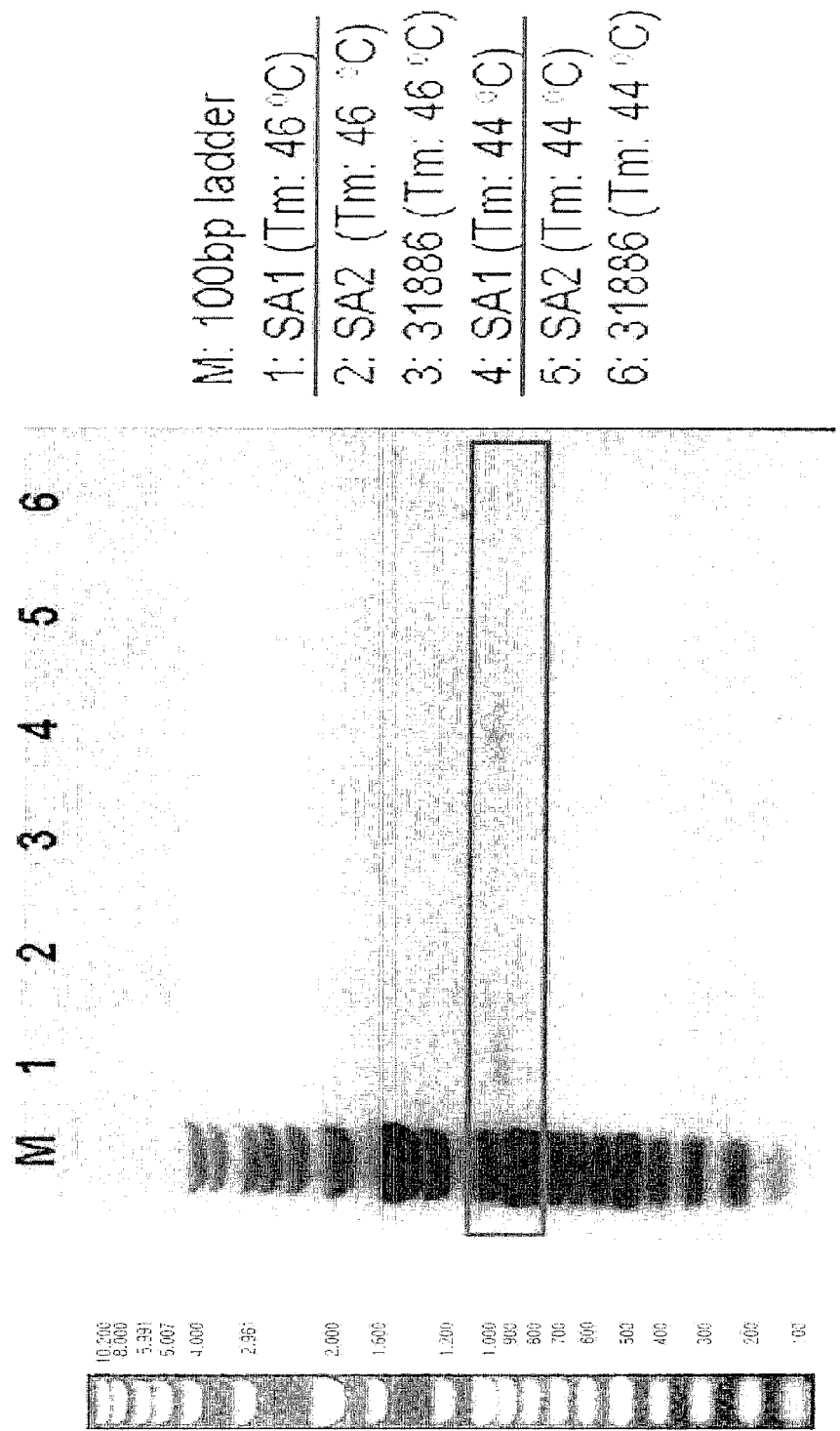
FIG. 5 is a photograph illustrating the result of PCR with ica C gene for the isolation of *Staphylococcus aureus* capable of forming biofilm.
Figure 6:
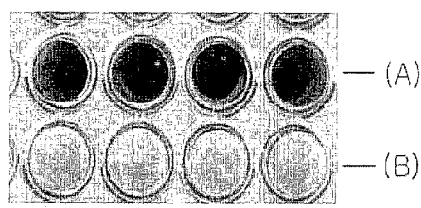
FIG. 6 is a photograph illustrating the formation of biofilm by the isolated SA1 *Staphylococcus aureus*. (A): control *Staphylococcus aureus* which is not able to form biofilm. (B): SA1 *Staphylococcus aureus* forming biofilm.

From the PCR, one of *Staphylococcus aureus* strain was confirmed to have ica C gene (named this *Staphylococcus aureus* as SA1) (FIG. 5). That is, this SA1 *Staphylococcus aureus* presumably has the ability to form biofilm. Then, biofilm formation by SA1 *Staphylococcus aureus* was examined. Precisely, SA1 *Staphylococcus aureus* was cultured in 5 ml. TSB medium containing 0.25% D-(+)-glucose for overnight. The culture broth of SA1 *Staphylococcus aureus* was diluted (1:50) with TSB medium containing D-(+)-glucose, which was disturbed in a 96-well plate (polystyrene, Corning) by 200 µl. The plate was shaking-cultured at 100 rpm for 24 hours in a 37° C. incubator. After 24 hours of the culture, 50 µl of TSB medium containing 0.25% D-(+)-glucose was added in each well of plate to supplement evaporated medium, followed by culture at 37° C. for 24 hours. Upon completion of the additional culture, each well was washed with 200 µl of PBS, followed by examination of the biofilm formation. As shown in FIG. 6, the selected SA1 *Staphylococcus aureus* formed biofilm.

<7-2> Biofilm Removal Activity

Figure 7:
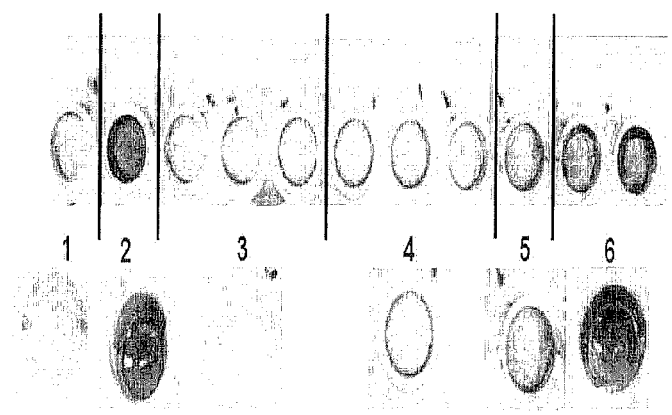
FIG. 7 is a set of photographs illustrating the elimination of biofilm formed by SA1 *Staphylococcus aureus* by the *bacteriophage* and lytic protein derived therefrom of the present invention. #1: sample treated with the lytic protein SAL-1 and then stained. #2: negative control sample stained without the treatment, #3: sample treated with the *bacteriophage* SAP-2 ant then stained, #4: sample treated with the lytic protein SAL-2 and then stained, #5: positive control sample treated with lysostaphin and then stained, and #6: sample treated with PBS alone and then stained. The quantity of each treatment component was not significantly considered. The upper photograph illustrates the whole 96-well plate and the lower photograph illustrates each well of the plate in detail.

The present inventors investigated if the *bacteriophage* or lytic protein derived from the *bacteriophage* of the present invention could destroy biofilm formed by SA1 *Staphylococcus aureus*, according to the method of Wu et al (biofilm plate assay. Antimicrob Agents Chemother 47: 3407-3414, 2003). Particularly, SA1 *Staphylococcus aureus* was cultured in 5 id TSB medium containing 0.25% D-(+)-glucose for overnight. The culture broth of SA1 *Staphylococcus aureus* was diluted (1:50) with TSB medium containing D-(+)-glucose, which was disturbed in a 96-well plate (polystyrene, Corning) by 200 µl. The plate was shaking-cultured at 100 rpm for 24 hours in a 37° C. incubator. After 24 hours of the culture, 50 µl of TSB medium containing 0.25% D-(+)-glucose was added in each well of plate to supplement evaporated medium, followed by culture at 37° C. for 24 hours. After the additional culture, the wells were washed with 200 µl of PBS. The *bacteriophage* suspension and the lytic protein solution were independently added to each well, which stood for 24 hours. 24 hours later, the medium was eliminated and each well was washed with PBS. After drying the plate, safranin staining was performed with 200 µl of 0.1% safranin for one hour, followed by examination of removal of biofilm. The results are shown in FIG. 7. In this example, it was confirmed that biofilm formed by SA1 *Staphylococcus aureus* was destroyed by *bacteriophage* SAP-1, *bacteriophage* SAP-2 and those lytic proteins derived from the two *bacteriophages*. The lytic protein solution was more effective in destroying biofilm than the *bacteriophage* suspension. That is, the lytic protein derived from *bacteriophage* is more effective in destroying biofilm than *bacteriophage* itself. Destruction of biofilm starts with breaking the extracellular matrix, suggesting that *bacteriophage* SAP-1, *bacteriophage* SAP-2 and those lytic proteins derived from the two *bacteriophages* are also effective in destroying extracellular matrix of biofilm.

EXAMPLE 8

Biofilm Formation Inhibiting Activity

Biofilm formation inhibiting activity of the composition containing *bacteriophage* or lytic protein derived from the *bacteriophage* was investigated by using medical catheter. The general medical catheter (silicone elastomer coated foley balloon catheter: Sewoonmedica Co. Ltd.) was cut into 1 cm pieces, resulting in 15 catheter pieces. 3 of them were treated with nothing and 12 of them were grouped again into four group 1 was treated with PBS containing *bacteriophage* SAP-1, group 2 was treated with PBS containing *bacteriophage* SAP-2, group 3 was treated with PBS containing SAL-1, the lytic protein derived from *bacteriophage* SAP-1 and group 4 was treated with PBS containing SAL-2, the lytic protein derived from *bacteriophage* SAP-2, on their surfaces. The concentration of *bacteriophage* in the composition containing *bacteriophage* was $1 \times 10^{10}$ pfu/ml and the concentration of lytic protein in the composition containing lytic protein was 0.005% (w/v). Surface treatment was performed by soaking those catheter pieces completely in the composition containing *bacteriophage* or the composition containing lytic protein (one hour). After the surface treatment, SA1 *Staphylococcus aureus* culture broth cultured by the method of Example <7-2> was diluted (1:50) with TSB medium containing D-(+)-glucose and this diluted solution was sprayed on the surface of the catheter pieces. At this time, lumen of the catheter was also sprayed. The catheter pieces were then incubated in clean bench at 37° C. for 24 hours using hybridization device. 24 hours later, to supplement evaporated medium, TSB medium containing 0.25% D-(+)-glucose was sprayed additionally, followed by incubation at 37° C. for 24 hours again. Upon completion of the additional incubation, the catheter pieces were cut to the direction of length, followed by washing with PBS. After washing, biofilm formation was investigated. The results are shown in table 5.

TABLE 5

| | Surface treatment method (soaking for 1 hour) | | | | |
|---|---|---|---|---|---|
| | Non-treated | Treated with bacteriophage SAP-1 containing composition | Treated with bacteriophage SAP-2 containing composition | Treated with SAL-1 containing composition | Treated with SAL-2 containing composition |
| Result | +++ | --- | --- | --- | --- |

"+" indicates biofilm formed, and "−" indicates biofilm not formed.

Three of these signs are maximum that can represent each experiment.

That is, "+++" indicates biofilm was formed on all of three catheter pieces and "---" indicates biofilm was not formed on any of these three catheter pieces.

For the surface-treatment, PBS containing *bacteriophage* or PBS containing lytic protein was used. Additional experiment was performed by the same manner as described above, except that the surface treatment was distinguished. That is, to treat surface in this additional experiment, synovial jelly widely used for the catheter injection containing the same concentration of *bacteriophage* or lytic protein derived from the *bacteriophage* was used instead of PBS. Unlike the above one-hour soaking, it was just smeared well this time. But, the result was consistent with that of previous experiment.

TABLE 6

Surface treatment method
(smeared with synovial jelly)

| | Non-treated | Treated with bacteriophage SAP-1 containing composition | Treated with bacteriophage SAP-2 containing composition | Treated with SAL-1 containing composition | Treated with SAL-2 containing composition |
|---|---|---|---|---|---|
| Result | +++ | --- | --- | --- | --- |

"+" indicates biofilm formed, and "−" indicates biofilm not formed.
Three of these signs are maximum that can represent each experiment.
That is, "+++" indicates biofilm was formed on all of three catheter pieces and "−−−" indicates biofilm was not formed on any of these three catheter pieces.

From the above results, it was confirmed that the biofilm formation by SA1 *Staphylococcus aureus* can be effectively inhibited by the compositions containing *bacteriophage* SAP-1, *bacteriophage* SAP-2 or the lytic proteins derived from the two *bacteriophages*. Therefore, the composition of the present invention can be effectively used as a medical cleaner and an environmental purifier including a disinfectant.

EXAMPLE 9

Application of the Composition of the Present Invention in the Treatment of Disease Caused by *Staphylococcus aureus* Infection 24 milk-cows with bovine mastitis caused by *Staphylococcus aureus* infection were selected as targets of the experiment examining the treatment effect on mastitis of *bacteriophage* SAP-1, *bacteriophage* SAP-2 or lytic proteins derived therefrom. The milk-cows were grouped into 8 groups (three cows per group), and group 1 was treated with PBS containing *bacteriophage* SAP-1 at the concentration of $1 \times 10^8$ pfu/ml. group 2 was treated with PBS containing *bacteriophage* SAP-2 at the concentration of $1 \times 10^8$ pfu/ml, group 3 was treated with PBS containing SAL-1 at the concentration of 0.005% (w/v), group 4 was treated with PBS containing SAL-2 at the concentration of 0.005% (w/v). group 5 was treated with PBS containing both of *bacteriophage* SAP-1 at the concentration of $1 \times 10^8$ pfu/ml and *bacteriophage* SAP-2 at the concentration of $1 \times 10^8$ pfu/ml, group 6 was treated with PBS containing both of SAL-1 at the concentration of 0.005% (w/v) and SAL-2 at the concentration of 0.005% (w/v), and group 7 was treated with PBS containing *bacteriophage* SAP-1 at the concentration of $1 \times 10^8$ pfu/ml, *bacteriophage* SAP-2 at the concentration of $1 \times 10^8$ pfu/ml, SAL-1 at the concentration of 0.005% (w/v) and SAL-2 at the concentration of 0.005% (w/v). Treatment was performed by every day injection through papilla, and the dose was 5 ml per injection. The control group (3 milk-cows) was treated with 5 ml of PBS alone by the same manner everyday. The treatment continued for 10 days, during which somatic cells included in milk taken from the cow was counted by the conventional method. Once mastitis is developed, leucocytes are increased to prevent the pathogen and dead leucocytes by the fight with the pathogen are called somatic cells herein. The somatic cells are composed of mammary epithelial cells, immune cells (lymphocytes), neutrophils, and monocytes. Direct microscope assay, the most common method, is used for somatic cell counting. Briefly, milk sample was smeared on 1 cm$^2$ of slide glass an dried, followed by staining. Then, somatic cells were directly counted under microscope. The number of somatic cells was multiplied by microscope coefficient to calculate somatic cell number in 1 ml of milk. The results are shown in below. In Table 7, mean value of three milk-cows in each group is presented and standard error is not provided because each value is not much different from the mean value.

TABLE 7

Treatment effect on disease caused by *Staphylococcus aureus* infection
(somatic cell number/1 ml of milk)

| | A | B | C | D | E | F | G | H |
|---|---|---|---|---|---|---|---|---|
| Before treatment | $4.6 \times 10^5$ | $5.1 \times 10^5$ | $4.8 \times 10^5$ | $4.7 \times 10^5$ | $5.0 \times 10^5$ | $5.1 \times 10^5$ | $4.9 \times 10^5$ | $5.1 \times 10^5$ |
| After treatment | $6.7 \times 10^5$ | $1.6 \times 10^5$ | $1.9 \times 10^5$ | $2.2 \times 10^5$ | $1.9 \times 10^5$ | $1.7 \times 10^5$ | $1.8 \times 10^5$ | $1.7 \times 10^5$ |

In the above table, A) indicates the result of the injection with PBS; B) indicates the result of the injection with PBS containing *bacteriophage* SAP-1; C) indicates the result of the injection with PBS containing *bacteriophage* SAP-2; D) indicates the result of the injection with PBS containing SAL-1, the lytic protein derived from *bacteriophage* SAP-1; E) indicates the result of the injection of PBS containing SAL-2, the lytic protein derived from *bacteriophage* SAP-2; F) indicates the result of the injection with PBS containing *bacte-* riophage SAP-1 and bacteriophage SAP-2; G) indicates the result of the injection with PBS containing SAL-1, the lytic protein derived from bacteriophage SAP-1 and SAL-2, the lytic protein derived from bacteriophage SAP-2 and H) indicates the result of the injection with PBS containing bacteriophage SAP-1, bacteriophage SAP-2, SAL-1, the lytic protein derived from bacteriophage SAP-1 and SAL-2, the lytic protein derived from bacteriophage SAP-2.

As shown in the above results, only injection with the composition containing bacteriophage or lytic protein derived from the bacteriophage of the present invention was significantly effective in the treatment of mastitis. Therefore, it was suggested that the composition containing bacteriophage or lytic protein derived from the bacteriophage of the present invention could be effective as well in the treatment of other infectious disease caused by Staphylococcus aureus. It was also confirmed that single treatment of each bacteriophage and lytic protein thereof was as effective as combined treatment of the bacteriophage and the lytic protein derived therefrom, but time for full effect was shorten by the combined treatment. The results of B)-E) of Table 7 were obtained on the 9th-10th day from the treatment and the results of F)-H) were obtained on the 7th-8th day from the treatment. Effective close used for F)-H) was greater than for B)-F). The concentration of bacteriophage used for F) was reduced to half to make the total amount of bacteriophage equal to that used for B) or C), followed by experiment by the same manner as described above. As a result, time for full effect was similar to that before reducing the concentration of bacteriophage but shorter than that of case B) or C). Therefore, the combined treatment might be more effective.

It was investigated whether Staphylococcus aureus isolated from the milk-cows with bovine mastitis could form biofilm by the same manner as described in Example <7-1>. Then, 6 milk-cows infected with the Staphylococcus aureus capable of forming biofilm were selected. The selected 6 milk-cows were grouped into three (2 per group). Group 1 was injected with the conventional antibiotics alone, and group 2 was injected with 5 ml of PBS containing bacteriophage SAP-1 at the concentration of 1×10$^8$ pfu/ml, bacteriophage SAP-2 at the concentration of 1×10$^8$ pfu/ml, SAL-1 at the concentration of 0.005% (w/v) and SAL-2 at the concentration of 0.005% (w/v) every day through papilla. Group 3 was injected with 5 ml of PBS containing bacteriophage SAP-1 at the concentration of 1×10$^8$ pfu/ml, bacteriophage SAP-2 at the concentration of 1×10$^8$ pfu/ml, SAL-1 at the concentration of 0.005% (w/v) and SAL-2 at the concentration of 0.005% (w/v) together with the conventional antibiotics every day through papilla. At that time, the composition of the present invention was first injected and then the conventional antibiotic was injected right after. The conventional antibiotic used herein was gentamycin cream widely used for the treatment of bovine mastitis. The antibiotic comprises 70 mg of gentamycin and 2.5 mg of dexametasone in each syringe. The results are as follows.

TABLE 8

Treatment effect on disease caused by biofilm-forming Staphylococcus aureus infection (somatic cell number/1 ml of milk)

| | A | B | C |
|---|---|---|---|
| Before treatment | 4.7 × 10$^5$ | 5.0 × 10$^5$ | 4.8 × 10$^5$ |
| After treatment | 4.3 × 10$^5$ | 1.8 × 10$^5$ | 1.7 × 10$^5$ |

In the above table, A) indicates the result of the injection with the conventional antibiotic alone; B) indicates the result of the injection with PBS containing two kinds of bacteriophages and two lytic proteins derived therefrom; and C) indicates the result of the injection with PBS containing two kinds of bacteriophages and two lytic proteins derived therefrom together with the conventional antibiotic.

As shown in the above results, the conventional antibiotic was not effective in the treatment of infectious disease caused by biofilm-forming Staphylococcus aureus, while the composition of the present invention demonstrated the treatment effect on biofilm-associated infectious disease caused by biofilm-forming Staphylococcus aureus. Therefore, the composition of the present invention is presumably effective in other biofilm-associated infectious diseases caused by biofilm-forming Staphylococcus aureus as well. The result of B) was obtained about 7 days after the treatment, but the result of C) was obtained about 6 days after the treatment. The time gap was not so significant but suggested that the combined treatment of the composition of the present invention and the conventional antibiotic might be more effective.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A composition for removing a biofilm formed by *Staphylococcus aureus*, comprising one or more of the *bacteriophage* or *bacteriophage* lytic protein selected from the group consisting of *bacteriophage* SAP-1 (Accession No: KCTC 11153BP), *bacteriophage* SAP-2 (Accession No: KCTC11154BP), lytic protein SAL-1 (SEQ ID NO:28), and lytic protein SAL-2 (SEQ ID NO:31).

2. The composition of claim 1, wherein the composition is a disinfectant, a medical cleaner, or an environmental purifier.

3. A pharmaceutical composition for treatment of disease caused by *Staphylococcus aureus* capable of forming biofilm, comprising one or more of the *bacteriophage* or *bacteriophage* lytic protein selected from the group consisting of *bacteriophage* SAP-1 (Accession No: KCTC 11153BP), *bacteriophage* SAP-2 (Accession No: KCTC11154BP), lytic protein SAL-1 (SEQ ID NO: 28), and lytic protein SAL-2 (SEQ ID NO: 31).

4. The pharmaceutical composition of claim 3, further comprising an antibiotic.

5. The pharmaceutical composition of claim 4, wherein the antibiotic is lysozyme, lysostaphin, methicillin, oxacillin, or vancomycin.

6. The pharmaceutical composition of claim 3, wherein the disease is mastitis, dermatitis, sepsis, suppurative disorder, food poisoning, pneumonia, osteomyelitis, impetigo, bacteremia, endocarditis, or enteritis.

7. The pharmaceutical composition of claim 3, wherein the pharmaceutical composition is a medicinal therapeutic agent or an antibacterial agent.

* * * * *

UNITED STATES PATENT AND TRADEMARK OFFICE
CERTIFICATE OF CORRECTION

PATENT NO.       : 8,377,431 B2                                   Page 1 of 1
APPLICATION NO.  : 12/677990
DATED            : February 19, 2013
INVENTOR(S)      : Yoon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 179 days.

Signed and Sealed this
First Day of September, 2015

Michelle K. Lee
*Director of the United States Patent and Trademark Office*